(12) United States Patent
Neumann

(10) Patent No.: US 12,087,428 B2
(45) Date of Patent: *Sep. 10, 2024

(54) SYSTEMS AND METHODS FOR GENERATING A BODY DEGRADATION REDUCTION PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

(*) Notice: Subject to any disclaimer, the term of this patent is extended or adjusted under 35 U.S.C. 154(b) by 512 days.

This patent is subject to a terminal disclaimer.

(21) Appl. No.: 17/387,430

(22) Filed: Jul. 28, 2021

(65) Prior Publication Data

US 2022/0208347 A1 Jun. 30, 2022

Related U.S. Application Data

(63) Continuation-in-part of application No. 17/136,283, filed on Dec. 29, 2020, now Pat. No. 11,139,064.

(51) Int. Cl.
*G16H 20/60* (2018.01)
*G06N 20/20* (2019.01)
(Continued)

(52) U.S. Cl.
CPC .............. *G16H 20/60* (2018.01); *G06N 20/20* (2019.01); *G16H 15/00* (2018.01); *G16H 20/70* (2018.01); *G16H 20/90* (2018.01); *G16H 70/20* (2018.01)

(58) Field of Classification Search
CPC .................. G06Q 50/22–24; G16H 20/60
See application file for complete search history.

(56) References Cited

U.S. PATENT DOCUMENTS 10,352,920 B2 * 7/2019 Ehrenkranz ............ A61K 33/18
2004/0001817 A1 * 1/2004 Giampapa .............. A61K 36/45
514/23

(Continued)

FOREIGN PATENT DOCUMENTS

CH 713713 A2 10/2018
WO WO-2015054694 A2 * 4/2015 ............. A61K 31/12
(Continued)

OTHER PUBLICATIONS

"Telomere Length and Aging: 5 ways to maintain healthy telomeres"; Life length; Nov. 26, 2018. (Year: 2018).*
(Continued)

*Primary Examiner* — John A Pauls
(74) *Attorney, Agent, or Firm* — Caldwell Intellectual Property Law

(57) ABSTRACT

System for generating a body degradation reduction program including a computing device configured to receive at least a degradation marker, retrieve a body degradation profile as a function of the at least a degradation marker, assign the body degradation profile to a degradation category, identify, using the degradation category and the body degradation profile, a plurality of lifestyle elements, wherein identifying the plurality of lifestyle elements includes calculating a plurality of lifestyle element amounts as a function of a respective effect of each of a plurality of lifestyle elements on the body degradation profile as a function of the degradation category, identifying the plurality of lifestyle elements as a function of the plurality of lifestyle element amounts, and generate a body degradation reduction program, using the plurality of lifestyle elements, wherein the body degradation reduction program includes a frequency and a magnitude of engagement of the plurality of lifestyle elements.

20 Claims, 11 Drawing Sheets

(51) Int. Cl.
*G16H 15/00* (2018.01)
*G16H 20/70* (2018.01)
*G16H 20/90* (2018.01)
*G16H 70/20* (2018.01)

(56) References Cited

U.S. PATENT DOCUMENTS

| | | | |
|---|---|---|---|
| 2005/0249821 A1* | 11/2005 | Paul | A61K 31/375 |
| | | | 514/474 |
| 2006/0269619 A1 | 11/2006 | Moneymaker | |
| 2007/0148699 A1* | 6/2007 | Friesen | G01N 33/5088 |
| | | | 435/7.1 |
| 2008/0161661 A1 | 7/2008 | Gizewski | |
| 2010/0021533 A1 | 1/2010 | Mazed | |
| 2010/0113892 A1 | 5/2010 | Kaput | |
| 2012/0040855 A1* | 2/2012 | Pan | C12Q 1/6881 |
| | | | 435/6.12 |
| 2012/0220488 A1* | 8/2012 | Li | A61P 9/00 |
| | | | 506/18 |
| 2015/0104523 A1 | 4/2015 | Lockwood | |
| 2015/0346220 A1 | 12/2015 | Frostegård | |
| 2017/0290516 A1* | 10/2017 | Nguyen | G16H 50/30 |
| 2018/0192945 A1 | 7/2018 | Diener | |
| 2018/0228840 A1* | 8/2018 | Veiga Chacón | C12N 5/0636 |
| 2019/0228840 A1* | 7/2019 | Kamens | G16B 40/20 |
| 2019/0267128 A1 | 8/2019 | Decombel | |
| 2020/0027557 A1 | 1/2020 | Karow | |

FOREIGN PATENT DOCUMENTS

| | | |
|---|---|---|
| WO | 2019087196 A1 | 5/2019 |
| WO | 2020146263 A1 | 7/2020 |
| WO | 2020210487 A1 | 10/2020 |

OTHER PUBLICATIONS

Title: Nutrigenetics, nutrigenomic and precision medicine Date: Sep. 2020 By: Meiliana.

Title: Association of Neurocognitive and Physical Function With Gait Speed in Midlife Date: Oct. 11, 2019 By: Rassmussen.

* cited by examiner

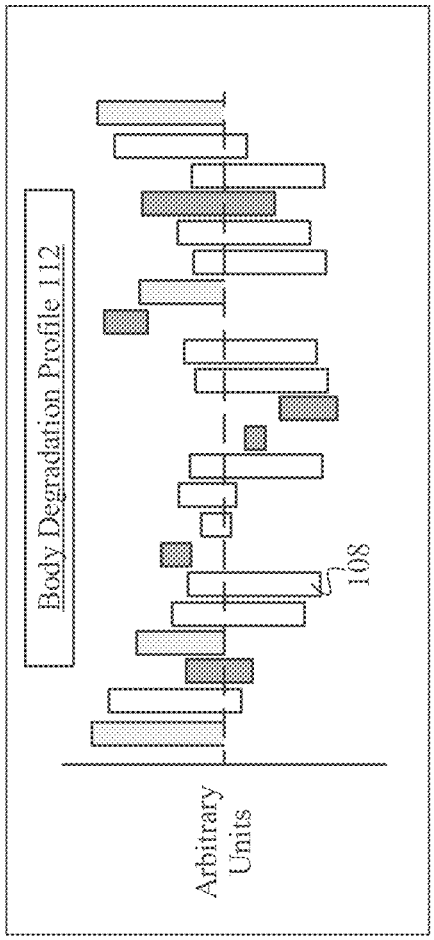
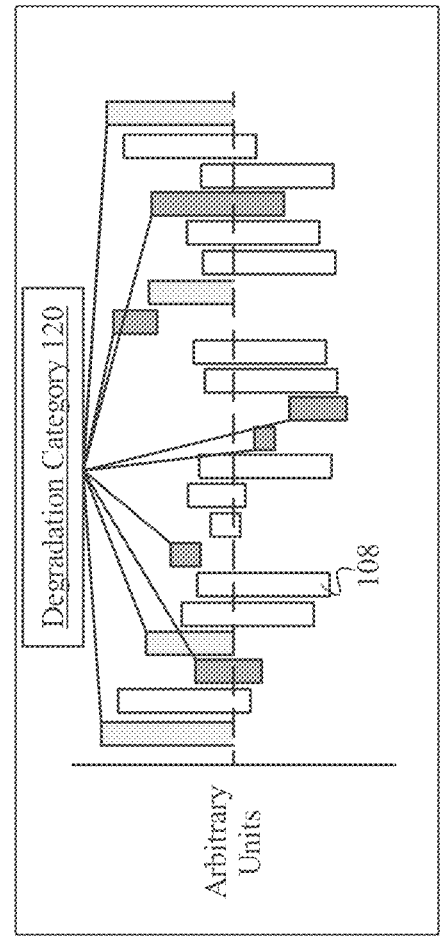

SYSTEMS AND METHODS FOR GENERATING A BODY DEGRADATION REDUCTION PROGRAM

CROSS-REFERENCE TO RELATED APPLICATIONS

This application is a continuation-in-part of Non-provisional application Ser. No. 17/136,283 filed on Dec. 29, 2020 and entitled "SYSTEMS AND METHODS FOR GENERATING A BODY DEGRADATION REDUCTION PROGRAM", the entirety of which is incorporated herein by reference.

FIELD OF THE INVENTION

The present invention generally relates to the field of nutrition planning for alleviating physiological degradation. In particular, the present invention is directed to systems and methods for generating a body degradation reduction program.

BACKGROUND

Efficient systems for tracking age-related biological degradations suffer from difficulties in adequately sampling the breadth of physiological parameters that relate to degradation over the lifetime of the user. Furthermore, systems encounter difficulty in efficiently and properly identifying the ways in which degradations occur, capturing the amounts of degradation and rates of degradation, and predicting degradation trajectories from these confounding variables.

SUMMARY OF THE DISCLOSURE

In an aspect, a system for generating a body degradation reduction program is presented. The system includes a computing device. The computing device is configured to receive at least a degradation marker related to a user, retrieve a body degradation profile as a function of the at least a degradation marker, assign the body degradation profile to a degradation category, and identify, using the degradation category and the body degradation profile, a plurality of lifestyle elements. Identifying the plurality of lifestyle elements includes calculating a plurality of lifestyle element amounts as a function of a respective effect of each of a plurality of lifestyle element amounts on the body degradation profile as a function of the degradation category and identifying the plurality of lifestyle elements as a function of the plurality of lifestyle element amounts. The computing device is configured to generate a body degradation reduction program using the plurality of lifestyle elements. Generating the body reduction program includes training a machine learning model. The machine learning model is trained by using a plurality of training data, wherein the plurality of training data comprising lifestyle element amounts and a respective effect of each of a plurality of lifestyle element amounts on the body degradation profile of a user. The machine learning model, responsive to training, is configured to provide a body degradation reduction program as a function of a respective effect of each of a plurality of lifestyle element amounts on the body degradation profile of a user. The computing device is configured to output on a graphical user interface, the body degradation reduction program. The body degradation reduction program includes a frequency of engagement of the plurality of lifestyle elements and a magnitude of engagement of the plurality of lifestyle elements.

In another aspect, a method for generating a body degradation reduction program is presented. The method includes receiving, by a computing device, at least a degradation marker related to a user, retrieving, by the computing device, a body degradation profile as a function of the at least a degradation marker, assigning, by the computing device, the body degradation profile to a degradation category and identifying, by the computing device, using the degradation category and the body degradation profile, a plurality of lifestyle elements. Identifying the plurality of lifestyle elements includes calculating a plurality of lifestyle element amounts as a function of a respective effect of each of a plurality of lifestyle elements on the body degradation profile as a function of the degradation category and identifying the plurality of lifestyle elements as a function of the plurality of lifestyle element amounts. The method includes generating, a body degradation reduction program using the plurality of lifestyle elements. Generating the body degradation reduction program includes training a machine learning model, wherein the machine learning model is trained by using a plurality of training data, the plurality of training data comprising lifestyle element amounts and a respective effect of each of a plurality of lifestyle element amounts on the body degradation profile of a user. The machine learning model, responsive to training, is configured to provide a body degradation reduction program as a function of a respective effect of each of a plurality of lifestyle element amounts on the body degradation profile of a user. The method includes outputting, on a graphical user interface, the body degradation reduction program, wherein the body degradation reduction program includes a frequency of engagement of the plurality of lifestyle elements and a magnitude of engagement of the plurality of lifestyle elements.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 4A and 4B are a diagrammatic representation of a body degradation profile;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a body degradation reduction program. In an embodiment, system includes a computing device configured to receive degradation markers of a user. Degradation markers may include experimental testing results, genotypic and phenotypic data, blood panel analysis, and the like. Computing device is configured to retrieve a degradation profile corresponding to the user. Computing device may generate degradation profile by using a machine-learning algorithm to model degradation markers to biological degradation. Computing device may classify the user to a degradation category, for instance using a machine-learning classifier according to subsets of degradation data from a plurality of users. Computing device is configured to determine the effect of nutrients on the user's body degradation profile and calculate nutrient amounts according to the effect that may prevent, or otherwise address, degradation markers identified of the user. Computing device may identify nutrition elements, such as an individual ingredients, and calculate nutrient amounts as a function of relationships derived between nutrient amounts and degradation. Computing device may accept user input via a user interface and generate a body degradation reduction program, wherein nutrition elements are curated by generating an objective function according to nutrition elements, the unique degradation profile, and constraints imposed by user input. Participation and adherence to reduction program may be provided a degradation score for tracking body degradation.

Figure 1:
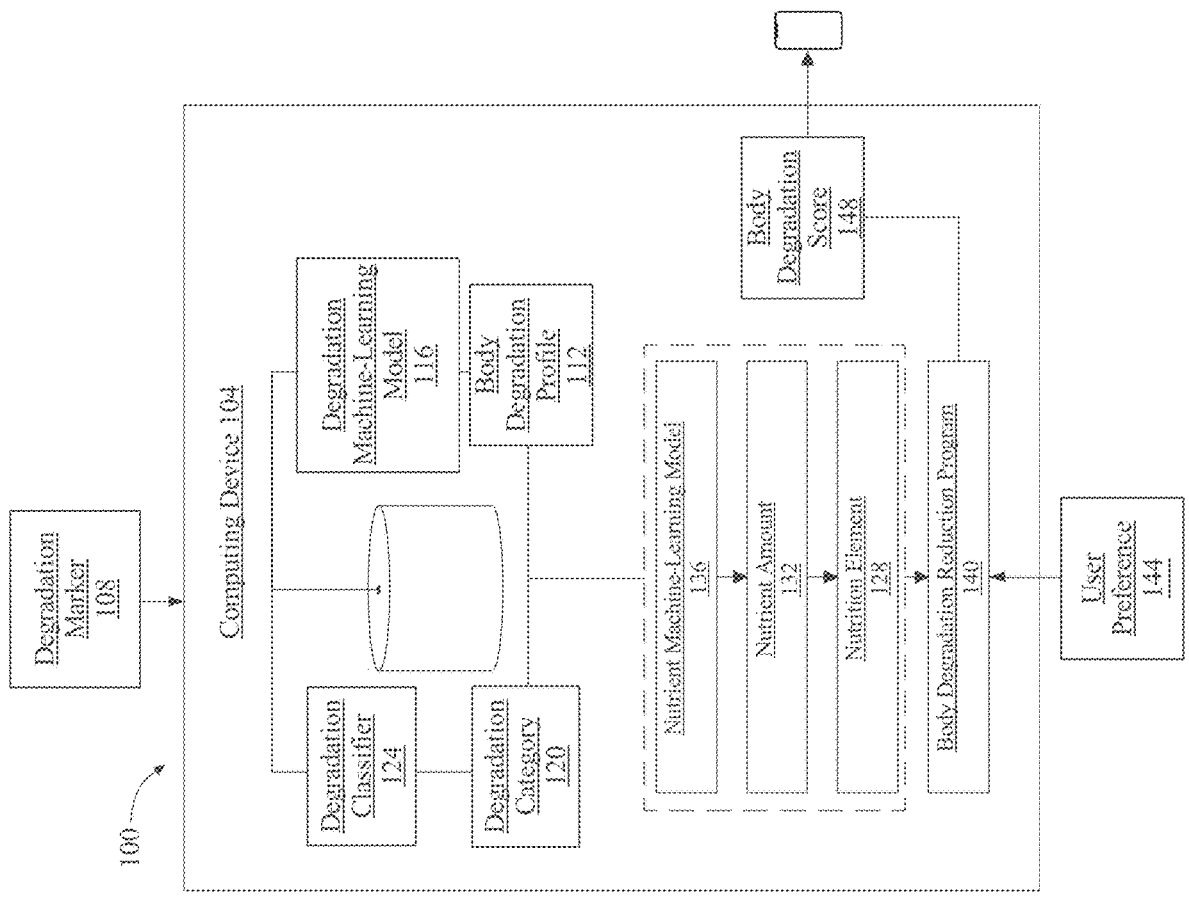
FIG. 1 is a block diagram illustrating a system for generating a body degradation reduction program.

Referring now to FIG. 1, an exemplary embodiment of a system 100 for generating a body degradation reduction program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software, and the like) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device is configured to receive at least a degradation marker related to a user. A "degradation marker," as used in this disclosure, is a biological and/or chemical substance or process that is indicative of the presence of biological degradation in the body. As used in this disclosure, "biological degradation," is a physiological deterioration indicative of biological aging. Degradation marker 108 may include receiving data indicative of biological degradation over the lifetime of the user, wherein degradation is physiological deterioration over time, as a consequence of biological aging. Degradation marker 108 may include biological molecules existing within a normal cell, a stressed cell, disease state cell, and/or a specific response of the body indicative of deterioration and/or aging. Receiving the at least a degradation marker 108 may include receiving a result of one or more tests relating the user. Degradation marker 108 may include test results of screening and/or early detection of degeneration, diagnostic procedures, prognostic indicators from other diagnoses, from predictors identified in a medical history, and physiological data and data relating to biomolecules associated with degradation such as physiological parameters including systolic and diastolic blood pressure, pulse pressure, pulse rate, peak expiratory flow, EKG data; blood metabolites such as homocysteine, creatinine, low-density lipoprotein (LDL), very low density lipoprotein (VLDL), high-density lipoprotein (HDL), triglycerides, fasting glucose, glycosylated hemoglobin (HbA1c); body compositional data including BMI, lean body mass, waist-to-hip ratio; hormonal profile including leptin, adiponectin, testosterone; immunological and disease state indicators such as c-reactive protein, IL-6, fibrinogen, albumin, TNF-$\alpha$, serum amyloid A, cytomegalovirus, Epstein Barr virus, T cell concentration/ratio, Amyloid B42, Total (t)-Tau, F2-isoprostanes (F2-iso), cortisol, DHEA-S, IGF-1; neurotransmitter concentration and balance such as for norepinephrine, epinephrine; biomarkers of organ function such as cystatin C; indicators of oxidative stress such as reactive oxygen species, superoxide dismutase; genotypic and epigenetic indicators of biological aging such as telomere length; among other data indicative of degradation. A person skilled in the art, having the benefit of the entirety of this disclosure, will be aware of various additional tests and/or data that may be used and or received as degradation marker 108.

Continuing in reference to FIG. 1, degradation marker 108 may include results and or analysis enumerating the identification of DNA sequences. Degradation marker 108 may include the presents of single nucleotide polymorphisms (SNPs), mutations, chromosomal deletions, inversions, translocation events, and the like, in genetic sequences. Degradation marker 108 may include epigenetic factors indicative of rates of degradation such as patterns of microRNAs (miRNAs). Degradation marker 108 may include hematological analysis including results from T-cell activation assays, abnormal nucleation of white blood cells, white blood cell counts, concentrations, recruitment and localization, and the like. Degradation marker 108 may be received as a function of a user indicating a prior diagnosis, treatment received, among other data indicated in a medical history, physical assessment, and the like. Degradation marker 108 may include any symptoms, side effects, and co-morbidities associated with and relating to aging, treatment regimens, recovery from injury and/or illness, and the like. Degradation marker 108 may be received and/or identified from a biological extraction of a user, which may include analysis of a physical sample of a user such as blood, DNA, saliva, stool, and the like, without limitation and as described in U.S. Nonprovisional application Ser. No. 16/886,647, filed May 28, 2020, and entitled, "METHODS AND SYSTEMS FOR DETERMINING A PLURALITY OF BIOLOGICAL OUTCOMES USING A PLURALITY OF DIMENSIONS OF BIOLOGICAL EXTRACTION USER DATA AND ARTIFICIAL INTELLIGENCE," the entirety of which is incorporated herein by reference.

Continuing in reference to FIG. 1, degradation marker 108 may be organized into training data sets. "Training data," as used herein, is data containing correlations that a machine learning process, algorithm, and/or method may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine learning processes as described in further detail below.

Continuing in reference to FIG. 1, degradation marker 108 may be used to generate training data for a machine-learning process. A "machine learning process," as used in this disclosure, is a process that automatedly uses a body of data known as "training data" and/or a "training set" to generate an algorithm (such as a collection of one or more functions, equations, and the like) that will be performed by a machine-learning module to produce outputs given data provided as inputs; this is in contrast to a non-machine learning software programing where the commands to be executed are determined in advance by a subject and written in a programming language, as described in further detail below.

Continuing in reference to FIG. 1, degradation marker 108 may be organized into training data sets and stored and/or retrieved by computing device 104, without limitation, as a relational database, a key-value retrieval database such as a NOSQL database, or any other format or structure for use as a database that a person skilled in the art would recognize as suitable upon review of the entirety of this disclosure. Degradation marker 108 training data may alternatively or additionally be implemented using a distributed data storage protocol and/or data structure, such as a distributed hash table and the like. Degradation marker 108 training data may include a plurality of data entries and/or records, as described above. Data entries may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries of degradation markers may be stored, retrieved, organized, and/or reflect data and/or records as used herein, as well as categories and/or populations of data consistent with this disclosure.

Continuing in reference to FIG. 1, computing device is configured to retrieve a body degradation profile related to the user. A "body degradation profile," as used in this disclosure, is a profile that captures the level of biological degradation of the user. Body degradation profile 112 may include at least a degradation rate of biological degradation, wherein the degradation level is a relative level of physiological integrity compared to theoretical level of physiological integrity according to what is scientifically achievable for an individual. A "degradation rate," as used in this disclosure, is a level of degradation change over time, as an individual ages. Body degradation profile 112 may include at least a degradation rate which may be an instantaneous rate or a rate that is over a variable range of time. Body degradation profile 112 may include biological degradation such as physiological deterioration of, for instance and without limitation, vision, hearing, cardiovascular endurance, maintenance of lean body mass, bone mineral density, short-term memory, mental plasticity, neurodegeneration, telomere length, and the like.

Continuing in reference to FIG. 1, body degradation profile 112 may include any number of degradation parameters. A "degradation parameter," as used in this disclosure, is a quantitative metric that encapsulates a biological degradation in the user according to the presence of at least a degradation marker 112. For instance and without limitation, a current state of degradation may include a degradation parameter that enumerates a current propensity for developing a neurodegenerative disease such as Alzheimer's disease, dementia, Parkinson's disease, among other neurodegenerative disorders, based on advanced physiological deterioration indicative a particular of degradation marker 108, such as tau protein expression, presence of α-synuclein plaques, Lewy bodies, and the like. A current state of degradation may include "no degenerative disorder". In individuals harboring no obvious degenerative disorder, a current state of degradation may include a tissue, organ, disease category, and the like, with which the user may most closely be classified, or have a likelihood of developing in the future. Degradation parameter may be degradation-specific, for instance and without limitation, a numerical value for each of 100+ types of physiological deterioration categories, where each numerical value communicates a likelihood that a degradation marker 108 relates to a particular disorder. Body degradation profile 112 may include any medical, physiological, biological, chemical, and/or physical determination about the current state of a user's propensity for disease according to body degradation, including projected, future likelihood for disease. Body degradation profile 112 may include qualitative and/or quantitative summarization of the presence of degradative symptomology, development of degenerative disease, biomarkers indicative of degeneration, current rates of degradation, future rates of degradation, lifetime risk associated with the current and future rates, biomarkers classified to subcategories, and the like. Body degradation profile 112 may include qualitative determinations, such as binary "yes"/"no" determinations for particular degradation types, "normal"/"abnormal" determinations about the presence of and/or concentration of degradation markers 108, for instance as compared to a normalized threshold value of a biomarker among healthy adults. Body degradation profile 112 may include a plurality of degradation parameters, wherein degradation parameters are quantitative determinations such as a "body degradation score", which may include any metric, parameter, or numerical value that communicates a level of body degradation. Body degradation profile 112 may include degradation parameters that are mathematical expressions relating the current degradation state.

Continuing in reference to FIG. 1, computing device 104 may retrieve body degradation profile 112 from a database. Database may be implemented, without limitation, as a relational database, a key-value retrieval database such as a NOSQL database, or any other format or structure for use as a database that a person skilled in the art would, upon the benefit of this disclosure in its entirety, may recognize as suitable upon review of the entirety of this disclosure. Database may include a degradation program database, as described in further detail below. Alternatively or additionally, database may be implemented using a distributed data storage protocol and/or data structure, such as a distributed hash table and the like. Database may include a plurality of data entries and/or records, as described herein. Data entries for body degradation profile 112 may be flagged with or linked to one or more additional elements of information, which may be reflected in data entry cells and/or in linked tables such as tables related by one or more indices in a relational database.

Continuing in reference to FIG. 1, retrieving body degradation profile 112 may include a process of searching for, locating, and returning body degradation profile 112 data. For example, body degradation profile 112 may be retrieved as documentation on a computer to be viewed or modified such as files in a directory, database, and the like. In non-limiting illustrative embodiments, computing device 104 may locate and download body degradation profile 112 via a web browser and the Internet, receive as input via a software application and a user device, and the like.

Continuing in reference to FIG. 1, retrieving body degradation profile 112 may include receiving data via a graphical user interface. A "graphical user interface," as used in this disclosure, is any form of a user interface that allows a user to interface with an electronic device through graphical icons, audio indicators, text-based interface, typed command labels, text navigation, and the like, wherein the interface is configured to provide information to the user and accept input from the user. Graphical user interface may accept input, wherein input may include an interaction (such as a questionnaire) with a user device. A user device, as described in further detail below, may include computing device 104, a "smartphone," cellular mobile phone, desktop computer, laptop, tablet computer, internet-of-things (IOT) device, wearable device, among other devices. User device may include any device that is capable for communicating with computing device 104, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Still referring to FIG. 1, retrieving the body degradation profile 112 related to the user may include training a degradation machine-learning model with the training data that includes a plurality of data entries wherein each entry correlates degradation markers to biological degradation. Computing device 104 may generate the body degradation profile 112 as a function of the degradation machine-learning model and at least a degradation marker 108. Degradation machine-learning model 116 may include any machine-learning process, algorithm, and/or model as performed by machine-learning module, described in further detail below. Generating body degradation profile 112 as a function of training data and a machine-learning model may be performed, without limitation, as described in Ser. No. 17/000,929, filed Aug. 24, 2020, titled "METHOD OF AND SYSTEM FOR IDENTIFYING AND AMELIORATING BODY DEGRADATIONS," the entirety of which is incorporated herein by reference. Relationships observed in training data to enumerate body degradation for body degradation profile 112 may be used to determine cross-body degradations, wherein degradation from one instance may be statistically related to body degradations for which no directly observable data exists, for instance and without limitation, as described in Ser. No. 17/000,973, filed Aug. 24, 2020, titled "A METHOD OF AND SYSTEM FOR IDENTIFYING AND ENUMERATING CROSS-BODY DEGRADATIONS," the entirety of which is incorporated herein by reference.

Continuing in reference to FIG. 1, training data for degradation machine-learning model 116 may include degradation markers 112 organized into training data sets, as described above, including results from biological extraction samples, health state questionnaires regarding symptomology, medical histories, physician assessments, lab work, and the like. Training data may be retrieved from a database, as described in further detail below. Body degradation profile 112 training data may originate from the subject, for instance via a questionnaire and a user interface with computing device 104, for user to provide medical history data and/or symptoms. Receiving body degradation profile training data may include receiving whole genome sequencing, gene expression patterns, and the like, for instance as provided by a genomic sequencing entity, hospital, database, the Internet, and the like. Body degradation profile 112 training data may include raw data values recorded and transmitted to computing device 104 via a wearable device such as a pedometer, gyrometer, accelerometer, motion tracking device, bio-impedance device, ECG/EKG/EEG monitor, physiological sensors, blood pressure monitor, blood sugar and volatile organic compound (VOC) monitor, and the like. Body degradation profile 112 training data may originate from an individual other than user, including for instance a physician, lab technician, nurse, dietician, strength coach, psychologist, and the like. It is important to note that training data for machine-learning processes, algorithms, and/or models used within system 100 herein may likewise originate from any source described for body degradation profile 112 training data.

Continuing in reference to FIG. 1, body degradation profile machine-learning model 116 may include any machine-learning algorithm such as K-nearest neighbors' algorithm, a lazy naïve Bayes algorithm, among other algorithms, machine-learning process such as supervised machine-learning, unsupervised machine-learning, or method such as neural nets, deep learning, and the like. Body degradation profile machine-learning model 116 may be trained to derive an equation, function, series of equations, or any mathematical operation, relationship, or heuristic, that can automatedly accept an input, such as degradation marker(s) 108, and correlate, classify, or otherwise calculate an output, such as degradation parameter(s). Body degradation profile machine-learning model 116 may include individual functions, derived for unique relationships observed from the training data for each degradation marker 108. In non-limiting illustrative examples, the parameters involved in a variety of physiological tests, as identified above, may be retrieved from a database, such as a repository of peer-reviewed research (e.g. National Center for Biotechnology Information as part of the United States National Library of Medicine), and the body degradation profile machine-learning model 116 may derive an algorithm which determines an average and statistical evaluation (mean±S.D.) calculated from the data, across which the user's parameters may be compared. In such an example, body degradation profile machine-learning model 116 may derive an algorithm according to the data used to derive the average and statistical evaluation changes as a function of the subset of data to which the user is to be compared, for instance and without limitation, based on age, fitness level, nutrition deficiency, symptomology, past diagnoses, and the like.

Continuing in reference to FIG. 1, computing device 104 is configured to assign the body degradation profile to a degradation category. A "degradation category," as used in this disclosure, is a determination about a current degradative state of the user as a function of a classification of the user according to subsets of a plurality of users. Degradation category 120 may include a designation of a degradation type. Degradation category 120 may include tissue and/or organ such as "kidney degradation", "liver degradation", "peripheral nervous system degradation", and the like. Degradation category 120 may include a designation regarding a degradation type that may not involve a particular tissue such as "vision degradation", "hearing degradation", "short term memory loss", and the like. Degradation category 120 may include pathological, histological, and/or clinical classification identifiers such as "telomeric length loss of >35 bp/year", "Mini-Mental State Exam (MMSE) score range of 20-24", "myelin sheath thinning", and the like. Degradation category 120 may include identifiers associated with disorders, conditions, symptoms, and the like, which may correspond with categorization. Degradation category 120 may include a predictive degradative classification, where a user such as a healthy young adult, does not harbor degradation marker(s) 108 indicative of obvious current degradation but may include data that indicates a degradation category 120 with which they may be most closely categorized to. For instance, a family history of vision loss as a function of aging due to a combination of epigenetic elements, lifestyle factors, and long-term nutritional impacts, may classify an individual in "vision degradation" degradation category 120, despite not currently exhibiting lessened vision acuity, astigmatism, or other loss of vision integrity. Body degradation profile 112 may have associated with it an identifier, such as a label, that corresponds to a degradation category 120. Degradation category 120 may be stored and/or retrieved from a database.

Continuing in reference to FIG. 1, assigning the body degradation profile 112 to a degradation category 120 may include training a degradation classifier using a degradation classification machine-learning process and training data which includes a plurality of data entries of body degradation profile data from subsets of categorized users. A "degradation classifier," as used in this disclosure, is a machine-learning classifier that sorts body degradation profile 112 to a degradation category 120. Degradation classifier 124 is generated by a degradation classification machine-learning process 128, which may include any machine-learning algorithm, process, and/or model described herein performed by a machine-learning module, as described in further detail below. Degradation classification machine-learning process 128 may generate degradation classifier 124 using training data. A classifier may include a machine-learning model, such as a mathematical model, neural net, or program generated by a machine learning algorithm known as a "classification algorithm," as described in further detail below. Degradation classifier 124 may sort inputs, such as body degradation profile 112, into categories or bins of data, such as classifying the data into degradation category 120, outputting the bins of data and/or labels associated therewith.

Continuing in reference to FIG. 1, training data for degradation classifier 124 may include a set of degradation markers 108 as it relates to classes of degradation types, organ and/or tissue types, ability types, and the like. For instance and without limitation, training data may include ranges of degradation markers 108 as they correlate to various degrees of vision loss, hearing integrity, maintaining musculoskeletal integrity, and the like. Such training data may include degradation markers 108 as it relates to degradation category 120 for subsets of a plurality of users, segmented according to user characteristics such as smoking, exercise, diet, age, sex, alcohol consumption, ethnicity, and the like. Training data may be used by classification machine-learning process to train a classifier to derive relationships present in the data that may result in a machine-learning model that automatedly classifies a user to a degradation category 120 as a function of the data present in their body degradation profile 112. Training data may originate from any source described herein, for instance retrieved from a database, retrieved via a web browser and the Internet, peer-reviewed research repository, clinical data, user input data, wearable device, physiological sensor, medical history data, and the like.

Continuing in reference to FIG. 1, degradation classifier 124 may be configured to output at least a datum that labels or otherwise identifies a set of data that are clustered together, found to be close, relate to one another via a metric, scoring, probability, and the like, as described below. Machine-learning module, as described in further detail below, may generate a classifier using a classification algorithm, defined as a process whereby computing device and/or any module and/or component operating thereon derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a body degradation profile 112 training data classifier may classify elements of training data to elements that characterizes a sub-population, including subset of degradation marker 108 such as gene expression patterns and epigenetic markers as it relates to a variety of degradation types and/or other analyzed items and/or phenomena for which a subset of training data may be selected.

Continuing in reference to FIG. 1, assigning the body degradation profile 112 to a degradation category 120 may include classifying the body degradation profile 112 to a degradation category 120 using the degradation classifier 124. Classification using degradation classifier 124 may include identifying which set of categories (degradation category 120) an observation (body degradation profile 112) belongs. Classification may include clustering based on pattern recognition, wherein the presence of degradation markers 108, such as genetic indicators, symptoms, and the like, identified in body degradation profile 112 relate to a particular degradation category 120. Such classification methods may include binary classification, where the body degradation profile 112 is simply matched to each existing degradation category 120 and sorted into a category based on a "yes"/"no" match. Classification done in such a manner may include weighting, scoring, or otherwise assigning a numerical value to elements in body degradation profile 112 as it relates to each body degradation type and assign a user to a degradation category 120 that results in the highest score. Such a score may represent a "likelihood", probability, or other statistical evaluation that relates to the classification into degradation category 120.

Continuing in reference to FIG. 1, computing device 104 may assign the degradation category 120 as a function of the classifying. Classifying the body degradation profile 112 (input) to a degradation category 120 (output) may include assigning the degradation category 120 as a function of the degradation classifier 124 generated by the degradation classification machine-learning process 128. Training data for degradation classifier 124 may include sets of degradation parameters and/or degradation markers 108, as described above, correlated to degradation category according to trends observed in the data for subsets of users. Such training data may be used to learn how to categorize a user's body degradation profile 112 to degradation categories depending on trends in the data. In this way, degradation classifier 124 may also generate new degradation categories depending on how well a user may "fit" within a particular classification.

Continuing in reference to FIG. 1, computing device 104 is configured to identify, using the body degradation profile 112, a plurality of nutrition elements for the user. A "nutrition element," as used in this disclosure, is an item that includes a nutrient intended to be used and/or consumed by user for reducing degradation. A "nutrient," as used in this disclosure, is any biologically active compound whose consumption is intended for addressing and/or reducing of degradation. Nutrition element 128 may include alimentary elements, such as meals (e.g. chicken parmesan with Greek salad and iced tea), food items (e.g. French fries), grocery items (e.g. broccoli), health supplements (e.g. whey protein), beverages (e.g. orange juice), and the like. Nutrition element 128 may be "personalized" in that nutrition elements are curated in a guided manner according to body degradation profile 112, degradation markers 108, user-designated symptoms, food allergies and/or intolerances, user preferences, and the like. Nutrition element 128 may include supplementary use of oral digestive enzymes and/or probiotics which may also have merit as anti-degradation measures. Nutrition elements 128 in a degradation prevention diet may include micronutrients such as vitamins, minerals, trace elements, electrolytes, such as selenium, folic acid, vitamin B-12, vitamin D, bicarbonate, calcium, and the like. Nutrition elements may include phytonutrients and plant-based macromolecules such as chlorophyll, antioxidants such as the carotenoids (α-carotene, β-carotene, lycopene, lutein, cryptoxanthin), and the like. Nutrient elements 120 may contain biologically active compounds that are not typically considered as part of recommended daily nutrients, nor are they intended to provide appreciable amounts of calories, such as phytonutrients, nutraceuticals, antioxidants, and the like; for instance and without limitation, *allium* and bioactive ingredients present in cruciferous vegetables such as broccoli sprouts, which are known sources of antioxidants such as sulforaphane. Nutrition elements 128 may include a specific dietary category, such as a "ketogenic diet", "low glycemic index diet", "Paleo diet", among others.

Continuing in reference to FIG. 1, identifying a plurality of nutrition elements 128 includes generating a plurality of nutrients that aid in reduction of body degradation as a function of the degradation category 120. Generating a plurality of nutrients may include querying for nutrients that are correlated to degradation category 120, for instance using a web browser and the Internet using the degradation category 120 as a search guide. Generating a plurality of nutrients may include retrieving nutrients correlated to degradation category 120 from a database, as described in further detail below.

Continuing in reference to FIG. 1, identifying a plurality of nutrition elements 128 includes determining a respective effect of each nutrient amount of the plurality of nutrients on the body degradation profile 112. An "effect of a nutrient,"

as used in this disclosure, is a change, consequence, and/or result in at least a degradation marker 108, body degradation profile 112, degradation category 120, and/or rate of biological degradation in a user due to consumption of an amount of a nutrient. An effect of a nutrient may be "no effect", "negligible effect", and/or "no calculated effect". Determining an effect of a nutrient may include determining how a degradation marker 108 may change, such as an increase/decrease according to a particular amount of nutrient. For instance and without limitation, such a determination may include calculating the effect of chronic, sustained nutrient amounts in a diet for weeks and/or months on epigenetic factors, blood serum levels of biomarkers, and the like. An effect may include changes in current rates and/or risk of degradation and/or future rates and/or risks of degradation.

Continuing in reference to FIG. 1, determining a respective effect of each nutrient amount of the plurality of nutrients may include retrieving the effects of the nutrient amount on the body degradation profile as a function of the at least a degradation marker 108. Computing device 104 may search for a nutrient effect using each degradation marker 108, and/or combination thereof, to locate and retrieve effects correlated to nutrients targeting a degradation marker 108. Retrieving an effect of a nutrient may include retrieving a hypothesis about the outcome for a user after consuming a nutrient amount and/or amount of a combination of nutrients. Such a hypothesis may include an equation, function, among other mathematical forms, for instance derived from empirical relationships between a nutrient and the physiological integrity of an organ, biological system, and the like. Retrieving an effect may include retrieving from a database, a research repository, or the like. Retrieving an effect may include, for instance, searching using the body degradation profile 112, a web browser, and the Internet, for a plurality of effects that nutrients may have. Retrieving an effect may include searching using the degradation category 120 for an effect of a nutrient on the type of degradation. In some embodiments, retrieving an effect may include calculating at least an effect, for instance by deriving a function from training data using a machine-learning algorithm.

Continuing in reference to FIG. 1, in non-limiting illustrative examples, determining an effect of a nutrient may include calculating if a change in degradation category 120 may arise from adding and/or removing a nutrient from a user's diet. For instance and without limitation, changing a degradation category 120 from "elevated skin degradation" to "reduced skin degradation" with increasing dietary vitamin E, vitamin K, and collagen by introducing nutrition elements 128 a user may not currently consume, such as vegetable oils, soybeans, tree nuts, seeds, green leafy vegetables, collagen supplements, and the like. Calculating an effect of a nutrient may include a mathematical operation, such as subtraction, addition, and the like. Calculating an effect of a nutrient may include retrieving an empirical equation that describes relationships between a nutrient and degradation marker 108, test results, degradation parameter, and the like. Calculating an effect of a nutrient may include deriving an algorithm, function, or the like, for instance using a machine-learning process and/or model. Calculating such an effect using machine-learning may include training data that includes a plurality of nutrients as it relates to effects on degradation categories 124, degradation markers 108, and the like.

Continuing in reference to FIG. 1, determining a respective effect of each nutrient amount of the plurality of nutrients may include generating a machine-learning model. Training data may include nutrient amounts correlated to their effect on the human body. For instance and without limitation, supplementation of amounts of fat-soluble vitamins, water-soluble vitamins, trace elements, minerals, electrolytes, among other nutrient categories in the diet may be correlated to renal function, liver function, vision integrity, bone mineral density, and the like. Such training data may originate from a database, research repository, clinical data, physician, plurality of users, or any other source described herein. Computing device 104 may generate a machine-learning model with such training data to derive an equation and/or function which describes relationships observed in the training data. Computing device 104 may then automatedly derive a respective effect for each nutrient, wherein the effect may become increasingly defined by parameters relating to the type of degradation in the user. The effect may also be related to an equation wherein, the magnitude of effect may be determined for all amounts of the nutrient. In this way, a particular nutrient amount may be determined based on the magnitude of effect desired.

Continuing in reference to FIG. 1, identifying a plurality of nutrition elements 128 includes calculating a plurality of nutrient amounts as a function of the respective effect of each of the plurality of nutrient amounts, wherein the plurality of nutrient amounts comprises a plurality of amounts intended to result in body degradation reduction corresponding to the degradation category 120. A "nutrient amount," as used in this disclosure, is a numerical value(s) relating to the amount of a nutrient. Nutrient amount 132 may include mass amounts of a vitamin, mineral, macronutrient (carbohydrate, protein, fat), a numerical value of calories, amounts of phytonutrients, antioxidants, probiotics, nutraceuticals, bioactive ingredients, and the like.

Continuing in reference to FIG. 1, calculating the plurality of nutrient amounts 132 may include generating training data using the plurality of predicted effects of the plurality of nutrient amounts 132. Training data may include retrieving effects on degradation for nutrients, as described above, and generating training data which includes nutrient amounts correlated to degradation category 120 the nutrient is intended to target. Training data may include nutrient identities correlated to particular body degradations, for instance vitamin A (retinol) correlated to vision degradation. Training data may include nutrient combinations from peer-reviewed studies correlated to body degradation, for instance potassium, folic acid, magnesium, zinc, and various dietary antioxidants in combination, which may reduce hearing loss in certain cohorts of users. Training data may include identified nutrient deficiencies in cohorts of users that may have particular body degradations at higher than normal rates. Training data may include nutrient surpluses in cohorts of users with less than normal rates of body degradation. Training data may originate from any source described herein, for instance and without limitation, from a physician, via user input from a plurality of users, a database, as described in further detail below, research repository, wearable device, physiological sensor, and the like.

Continuing in reference to FIG. 1, calculating the plurality of nutrient amounts 132 may include training a nutrient machine-learning model according to the training data, wherein training data includes a plurality of data entries that correlates the magnitude of nutrient effect to a plurality of nutrient amounts for each degradation category 120. Nutrient machine-learning model 136 may include any machine-learning process, algorithm, and/or model described herein as performed by machine-learning module described in further detail below. Nutrient machine-learning model 136 may be trained with training data that includes a plurality of data entries that includes nutrient effects, including the magnitude of effect, effects in combination with other nutrients, or the like, correlated to degradation category 120. Data may be correlated to degradation category 120 in that it is correlated to particular degradation markers 108, symptom alleviation, may be found in a subset of healthy adults, among other correlations. In this way, nutrient machine-learning model 136 may derive equations, functions, among other heuristics, which describe relationships observed in the training data regarding the full spectrum of nutrient amounts 132 targeted to the user's degradation category 120 and degradation markers 108.

Continuing in reference to FIG. 1, computing device may calculate the plurality of nutrient amounts 132 as a function of the nutrient machine learning model 136 and the degradation category 120. Computing device 104 may accept an input of a degradation category 120 relating to user and output a plurality of nutrient amounts 132 for the user as a function of the nutrient machine-learning model 136.

Continuing in reference to FIG. 1, computing device 104 is configured for calculating each of the nutrient amounts of the plurality of nutrient amounts as a function of the respective effect of each the plurality of nutrient amounts, wherein the plurality of nutrient amounts comprises a plurality of amounts intended to result in degradation alleviation corresponding to the degradation category. Calculating nutrient amounts, may include determining an effect of a nutrient on the plurality of degradation parameters in the body degradation profile 112, wherein the effect of the nutrient is correlated to the degradation parameter.

Continuing in reference to FIG. 1, computing device 104 may calculate nutrient amounts 132, for instance, by retrieving a default amount from a database. Computing device 104 may retrieve standard nutrient amounts, such as from a standard 2,000 calorie diet, and alter the amount according to a numerical scale associated with degradation markers 108 in the body degradation profile 112. Such a calculation may include a mathematical expressing using operations such as subtraction, addition, multiplication, and the like, for instance an equation that assigns a variable to the users body weight, level of degradation in the body degradation profile 112, and retrieves a start value of a vitamin and alters the amount using the mathematical expression. Alternatively or additionally, such a calculation may involve deriving a loss function, vector analysis, linear algebra, system of questions, among other mathematical heuristics, depending on the granularity of the process. Deriving such a process for calculating nutrient amounts may include machine-learning, as described above. Nutrient amounts 132 may include threshold values, or ranges of values, for instance and without limitation, between 80-120 mg vitamin C per 24 hours, wherein the range changes as a function of body degradation profile 112. Nutrient amounts 132 may be calculated as heat maps (or similar mathematical arrangements), for instance using banding, where each datum of body degradation profile 112 elicits a particular range of a particular nutrient amount 132 or set of amounts. In non-limiting illustrative examples, such a calculation may include querying for and retrieving a standard amount of water soluble vitamins for a healthy adult, for instance as described below in Table 1:

TABLE 1

| Nutrient | Amount |
|---|---|
| Vitamin C | 60 mg/day |
| Thiamin (B1) | 0.5 mg/1,000 kcal; 1.0 mg/day |
| Riboflavin (B2) | 0.6 mg/1,000 kcal; 1.2 mg/day |
| Niacin (B3) | 6.6 NE/1,000 kcal; 13 ND/day |
| Vitamin B6 | 0.02 mg/1 g protein; 2.2 mg/day |
| Vitamin B12 | 3 µg/day |
| Folic Acid | 400 µg/day |

Continuing in reference to FIG. 1, in reference to Table 1 above, wherein NE is niacin equivalent (1 mg niacin, or 60 mg tryptophan), mg (milligram), kcal (1000 kcal=1 Calorie), and µg (microgram). Computing device 104 may store and/or retrieve the above standard nutrient amounts 132, for instance in a database. The amounts may be re-calculated and converted according to a user's body degradation profile 112. For instance, these amounts may relate to an average BMI, healthy adult male, for any range of calories, but may be adjusted according to unique user-specific degradation markers 108. In non-limiting illustrative examples, a geriatric woman who is on a 1,400 Calorie/day diet, with onset of osteoporosis, vision loss, and advanced reduction in mental plasticity. In such an example, nutrient amounts 132 may be curated according to identified risk factors (degradation markers 108) and the above nutrient amounts 132 may be recalculated, where some amounts may increase, some may decrease, and some may remain constant.

Continuing in reference to FIG. 1, calculating nutrient amounts 132 may include deriving a weighting factor to adjust, or otherwise re-calculate, an amount. Weighting factor may be determined by computing device 104, for instance, by querying for vitamin amounts according to data inputs identified in the body degradation profile 112. For instance in non-limiting illustrative examples, if body degradation profile 112 indicates the presence of advanced telomere shortening as indicated from increase expression of stathmin-family genes, EF-1a, and p16, the biomarkers of telomeric dysfunction and DNA damage in cells. Telomere shortening is a natural process of the loss of chromosomal genetic material from the ends of chromosomal DNA which accumulates as an organism ages; telomere shortening in the genetic disorder, dyskeratosis congenita, is associated with an early onset of several age-associated disorders and reduced lifespan. Relationships may be found in nutrient amounts 132 relating to the slowing of telomere shortening, specifically in supplementing the diet with specific foods items such as legumes, nuts, seaweed, fruits, dairy products, and coffee, whereas it may be inversely associated with consumption of alcohol, and certain animal products such as red meat and/or processed meat. Although, vitamins found in such foods from organic sources may be superior from nonorganic sources, such as from commercially-available supplements, from a bioavailability standpoint. Additionally, per-user pharmacokinetics, rates of metabolism and/or adsorption of nutrients may differ user-to-user, which may negate the effectiveness of proscribing particular diet types and nutrition elements 128 to users. In such an instance, computing device 104 may account for such details using machine-learning to derive more specific nutrient amount 132 calculations and to more accurately calculate the amounts by which to increase/decrease nutrients found in such foods as a function of a user's telomere shortening as evidence by the presence of degradation markers 108. Therefore, computing device 104 may derive weighting factors to account for particular gene expression patterns, organic vs non-organic sources, and the food types with which the nutrients may originate.

Continuing in reference to FIG. 1, in non-limiting illustrative examples, computing device 104 may use a machine-learning process to perform a machine-learning algorithm to derive per-user pharmacokinetics, for instance of vitamin B6. The machine-learning algorithm may accept an input of numerical values including the total amount of protein consumed (in grams), total amount of vitamin B6 consumed (in mg) per day in a diet, and serum levels of the vitamin B6 vitamer, pyridoxal-5-phosphate, over the course of a month, and derive the rates of metabolism, or how 'well' the user is obtaining the vitamin from nutrition elements 128 and adsorbing vitamin B6. In other words, the algorithm may derive a function such as using linear regression, vector quantization, least squares, among other algorithms, that describes the pharmacokinetics for that particular user regarding what amount of vitamin B6 consumed, per amount of dietary protein, results in what corresponding amount of bioactive vitamin compound, as measured by the blood vitamer from a biological extraction. Such a function, derived from machine-learning, may then be used by computing device 104 with an input of the body degradation profile 112, which enumerates degradation markers 108, to calculate an output which is a more accurate, customized, per-user nutrient amount 132 of vitamin B6. Persons skilled in the art, upon benefit of this disclosure in its entirety, may appreciate that this process may be repeated for the full spectrum of nutrients, both required as part of a diet and not required as part of a diet, to control for specific metabolic differences in a population.

Continuing in reference to FIG. 1, additionally, in non-limiting illustrative examples, computing device 104 may relate the concentrations of the metabolic products related to vitamins (e.g. vitamers), minerals, phytonutrients, probiotics, antioxidative compounds, biologically activity ingredients, prodrugs, and the like, to their effective concentrations in tissues related to various degradation categories 124 in body degradation profile 112. For instance, computing device 104 may additionally search and retrieve data that relates the blood levels of the vitamin B6 vitamer, pyridoxal-5-phosphate, to the effective concentrations of vitamin B6 in the liver, which is particularly sensitive to aberrations in telomere loss. Computing device 104 may store and/or retrieve values in a "look-up table", or graph a relationship as a mathematical function, among other ways of representing a data structure that relates the data identified in the search. Alternatively or additionally, computing device 104 may derive a function, for instance using machine-learning, which correlates the concentration of a compound in a particular biological extraction, such as blood, to varying amounts in tissues such as breast tissue, liver, kidneys, and the like This may prove helpful in calculating nutrient amounts 132 as a function of user consumption to specific target nutrient amount 132 quantities within a particular organ/tissue according to the input data in the body degradation profile 112.

Continuing in reference to FIG. 1, computing device 104 is configured to identify the plurality of nutrition elements 128 as a function of the plurality of nutrient amounts 132. Identifying the plurality of nutrition elements 128 may include retrieving nutrition elements that include at least a nutrient amount of the plurality of nutrient amounts 132. Computing device 104 may accept an input of at least a nutrient amount 132 and retrieve nutrition elements 128 by searching a database for nutrition elements according to the nutrient and the amount. Computing device 104 may accept an input of nutrient amount 132 and may search using a web browser and the Internet for nutrition elements 128 according to the nutrient and its amount.

Continuing in reference to FIG. 1, identifying the plurality of nutrition elements 128 may include identifying the nutrition elements 128 according to the degradation category 120. Identifying nutrition element 128 according to degradation category 120 may include querying, for instance using a web browser and the Internet, for foods, supplements, bioactive ingredients, and the like, which are correlated with a particular degradation category 120. For instance and without limitation, computing device 104 may organize a search for foods intended for "musculoskeletal degradation", wherein an entire diet may be crafted around target nutrient amounts 132 and the categorization of the body degradation profile 112 to "musculoskeletal degradation". In such an example, the nutrition elements 128 are outputs generated from an input search criteria of "musculoskeletal degradation". The output elements become "personalized" as they are arranged into daily, weekly, monthly, and the like, individual meals and/or meal schedule according to a user's particular calculated nutrient amounts 132. The degradation category 120 may serve as a filtering step, wherein a search is guided by the body degradation profile 112 as it was classified to a degradation type.

Continuing in reference to FIG. 1, identifying the plurality of nutrition elements 128 may include generating combinations of located nutrition elements as a function of fulfilling the plurality of nutrient amounts 132. Computing device 104 may identify the plurality of nutrition elements 128 by using nutrient amount 124 as an input and generating combinations, lists, or other aggregates of nutrition elements 128 necessary to achieve nutrient amount 124. For instance, computing device 104 may use a template nutrient amount 124 of '200 mg vitamin C' and build a catalogue of nutritional elements 120 until the 200 mg vitamin C value is obtained. Computing device 104 may perform this task by querying for food items, for instance from a menu, grocery list, or the like, retrieving the vitamin C content, and subtracting the value from the nutrient amount 124. In non-limiting illustrative examples, computing device 104 may identify orange juice (90 mg vitamin C/serving; 200 mg-90 mg=110 mg) for breakfast, Brussel sprouts (50 mg vitamin C/serving; 110 mg-50 mg=60 mg) for lunch, and baked potato (20 mg vitamin C/serving) and spicy lentil curry (40 mg vitamin C/serving; 60 mg-(20 mg+40 mg)=0 mg) for dinner. In such an example, computing device 104 may search according to a set of instructions such as food preferences, allergies, restrictions, and the like, provided by a physician, medical history, user input, among other sources, and subtract each identified nutrition element 128 nutrient from nutrient amount 124 until a combination of nutritional elements 120 that represents a solution is found. Once a solution is found, computing device 104 may generate a file of nutrition elements 128 and store in a database, as described in further detail below. In this way, computing device 104 may generate customized meals, health shakes, recipes, and the like.

Continuing in reference to FIG. 1, computing device 104 is configured to generate a body degradation reduction program, using the plurality of nutrition elements 128, wherein the body degradation reduction program includes a frequency and a magnitude for reducing body degradation in the user. A "body degradation reduction program," as used in this disclosure, is a functional program and/or instruction set that provides instruction relating to one or more areas of a user's life, including but not limited to, physical fitness, stress management, meditation, spirituality, religion, energy healing, professional endeavors, personal endeavors, body, mind, health, finances, recreation, romance, personal development, and the like. A body degradation reduction program may include a collection of nutrient amounts 132 and nutrition elements 128 for reducing of body degradation. Body degradation reduction program 140 may be organized into a frequency (timing) and magnitude (serving size) schedule. A "frequency," as used in this disclosure, is a number of consumption occurrences associated with a time course, such as daily, weekly, monthly, and the like, of which a nutrition element is intended to be consumed. Frequency may be determined as a function of the identified effect, wherein the frequency of consumption is tailored to provide a sufficient minimal nutrient level over a time. A "magnitude," as used in this disclosure, is a serving size of at least a nutrition element as a function of the identified effect. Identifying the magnitude associated with a nutrition element may include calculating a serving size of the at least a nutrition element as a function of the identified effect. Body degradation reduction program 140 may include gathering, classifying, or otherwise categorizing nutrient amounts 132 and/or nutrition elements 128 lists, which incorporates degradation-specific recommendations. For instance, nutrition elements 128 may be scored with a numerical score scale that associates a meal, beverage, supplement, and the like, with preventing degradation, benefit to degradative symptoms, and the like. Body degradation reduction program 140 may include selecting nutrition elements 128 according to a threshold score, where items above the threshold are selected and arranged into meals. Threshold score may include a daily threshold, wherein nutrition elements 128 are selected each day according to the threshold; and threshold may include a numerical value relating to degradation prevention, a calculated nutrient amount 132, among other outputs of system 100 described herein. Determining body degradation reduction program 140 may include machine-learning. For instance and without limitation, training a machine-learning model to identify a scoring rubric for building the body degradation reduction program 140 based on some criteria such as preventing future degradation, alleviating symptoms, among other criteria. Body degradation reduction program 140 may relate specific degradation category 120 to specific nutrients of interest and provide nutrition element 128 scheduling times and serving sizes for each meal. Body degradation reduction program 140 may differ from one user to the next according to the magnitude of the disease outline (degradation category 120 and body degradation profile 112).

Continuing in reference to FIG. 1, generating the body degradation reduction may include receiving a user preference. A "user preference", as used in this disclosure, is a user input that designates a preference related to at least a nutrition element 128. User preference 144 may include designations of nutrition elements 128 to avoid and/or include such as particular food groups, condiments, spices, dietary restrictions such as 'no animal products', cuisine type such as 'Mediterranean foods', time of day for eating such as 'fasting before 10 am', and the like. User preference 144 may include indications of allergies, food intolerances, and the like, which may represent constraints on curating nutrition elements 128. In this way, computing device 104 may accept an input of user preference 144 filter, sort, classify, or otherwise modify the data structure of nutrition elements 128 and schedule the nutrition elements 128 into body degradation reduction program 140 in a custom, per-user manner. Computing device 104 may modify the plurality of nutrition elements 128 as a function of the user preference 144, for instance by providing recipes with steps omitted, new steps added, or entirely new recipes altogether utilizing the same or different nutrition elements 128. Computing device 104 may modify the plurality of nutrition elements 128 as a function of the user preference 144 by generating a new file, based on the preference, and storing and/or retrieving the file from a database, as described in further detail below.

Continuing in reference to FIG. 1, generating the body degradation reduction program 140 may include generating an objective function with the at least a plurality of nutrition elements 128 wherein the objection function outputs at least an ordering of a plurality of nutrition elements according to constraints from the degradation category 120 and the user preference 144. An "objective function," as used in this disclosure, is a mathematical function that may be used by computing device 104 to score each possible combination of nutrition elements 128, wherein the objective function may refer to any mathematical optimization (mathematical programming) to select the 'best' element from a set of available alternatives. Selecting the 'best' element from a set of available alternatives may include a combination of nutrition elements 128 which achieves the nutrient amounts 132 in addressing body degradation profile 112 in a user.

Continuing in reference to FIG. 1, an objective function may include performing a greedy algorithm process. A "greedy algorithm" is defined as an algorithm that selects locally optimal choices, which may or may not generate a globally optimal solution. For instance, computing device 104 may select combinations of nutrition elements 128 so that values associated therewith are the best value for each category. For instance, in non-limiting illustrative example, optimization may determine the combination of the most efficacious 'serving size', 'timing of consumption', 'probiotic product', 'vegetable', 'nutrient amount per meal', among other categories to provide a combination that may include several locally optimal solutions but may or may not be globally optimal in combination.

Still referring to FIG. 1, objective function may be formulated as a linear objective function, which computing device 104 may solve using a linear program, such as without limitation, a mixed-integer program. A "linear program," as used in this disclosure, is a program that optimizes a linear objective function, given at least a constraint; a linear program may be referred to without limitation as a "linear optimization" process and/or algorithm. For instance, in non-limiting illustrative examples, a given constraint might be a metabolic disorder of a user, as indicated by user preference 144, and a linear program may use a linear objective function to calculate combinations, considering how these limitations effect combinations. In various embodiments, system 100 may determine a set of instructions towards addressing a subject's body degradation profile 112 that maximizes a total degradation prevention score subject to a constraint that there are other competing objectives. For instance, if achieving one nutrient amount 124 by selecting from each nutrition element 128 may result in needing to select a second nutrition element 128, wherein each may compete in degradation prevention (e.g. adopting two or more diet types simultaneously may not be feasible, a vegan option and a non-vegan option, and the like). A mathematical solver may be implemented to solve for the set of instructions that maximizes scores; mathematical solver may be implemented on computing device 104 and/or another device in system 100, and/or may be implemented on third-party solver.

With continued reference to FIG. 1, objective function may include minimizing a loss function, where a "loss function" is an expression of an output of which a process minimizes to generate an optimal result. For instance, achieving nutrient amounts 132 may be set to a nominal value, such as '100', wherein the objective function selects elements in combination that reduce the value to '0', wherein the nutrient amounts 132 are '100% achieved'. In such an example, 'maximizing' would be selecting the combination of nutrition elements 128 that results in achieving nutrient amounts 132 by minimizing the difference. As a non-limiting example, computing device 104 may assign variables relating to a set of parameters, which may correspond to degradation prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 1, computing device 104 may use calculated nutrient amounts 132 from nutrient machine-learning model 136 to determine nutrition elements 128 more precisely. For instance, computing device 104 may retrieve a variety of nutrition elements 128 which contain particular vitamins, minerals, anti-inflammatory molecules, phytonutrients, antioxidants, bioactive molecules, and the like, which do not violate any other degradation prevention information associated with body degradation profile 112. Computing device 104 may mix-and-match nutrition elements 128 to arrive at a particular calorie amount, or range of calories, while achieving nutrient amounts 132.

Continuing in reference to FIG. 1, generating the body degradation reduction program 140 may include generating a degradation program classifier using a degradation program classification machine-learning process to classify nutrition elements 128 to the plurality of nutrient amounts 132, and outputting the plurality of nutrition elements as a function of the degradation program classifier. Degradation program classifier may include any classifier, as described above, generated by a classification machine-learning process using training data, performed by a machine-learning module as described in further detail below. Training data for degradation program classifier may include sets of data entries that include nutrition elements 128 that are correlated to nutrient amounts 132 that classifier may be trained to automatedly locate, sort, and output nutrition elements 128 according to calculated nutrient amounts 132 for the user. Such training data may originate via a database, the Internet, research repository, and the like, as described above for training data for other machine-learning processes. Training data may include foods, supplements, probiotics, nutraceuticals, and the like, correlated to nutrition facts, medicinal qualities, and the like, which a classifier may be trained to locate relationships that aid in locating nutrition elements 128. Degradation program classifier may accept an input of nutrient amounts 132 and output a plurality of nutrition elements 128 with associated frequency (timing) and dosage (serving size) schedule according to relationships between nutrition elements 128 and nutrient amounts 132. For instance and without limitation, degradation program classifier may identify relationships between individual fruits and vegetables, that when more vegetables are selected, certain fruits may not be necessary to schedule within the same timeframe. Such a classification process may determine a function, system of equations, and the like, which can be solved for in determining which nutrition elements 128 are useful toward obtaining the nutrient amounts 132, while not missing some lower limits of nutrient amounts 132 (trace elements) and not exceeding upper limits for other nutrient amounts 132 (calories).

Continuing in reference to FIG. 1, body degradation reduction program includes a body degradation score. A "body degradation score," as used in this disclosure, reflects the level of user participation in the body degradation reduction program 140 and the level of body degradation in the user as a function of adherence to body degradation reduction program 140. Body degradation score may include a numerical value, metric, parameter, and the like, described by a function, vector, matrix, or any other mathematical arrangement. Body degradation score 148 may include enumerating a user's current nourishment as it relates to body degradation alleviation, degradation rate, and/or degradation prevention. Generating body degradation score 148 may include using a machine-learning process, algorithm, and/or model to derive a numerical scale along which to provide a numerical value according to a user's body degradation profile 112 and participation in body degradation reduction program 140 generated from body degradation profile 112. For instance, such a machine-learning model may be trained with training data, wherein training data contains data entries of nutrient amounts 132 correlated to degradation prevention. Such a machine-learning model may be trained with said training data to be used by computing device 104 to correlate the consumption of particular foods in body degradation reduction program 140 to achieving some level of nutrient amount 132, and how the nutrient amount 132 relates to body degradation alleviation, degradation rate, and/or degradation prevention. Training data for a machine-learning model for generating body degradation score 148 may include a plurality of data entries including nutrient amounts correlated to effects on degradation, wherein the trained model may accept inputs of nutrition elements a user have consumed and automatedly determine how the score should increase and/or decrease based on the nutrient targets for the user. Such training data may originate from any source as descried above, such as a database, web browser and the Internet, physician, peer-reviewed research, and the like.

Continuing in reference to FIG. 1, in non-limiting illustrating examples, falling short of selenium and B vitamin nutrient amounts 132, may have a particular effect on body degradation score 148 for an individual who has been classified to a certain degradation category 120. Where, chronically falling short of the nutrient amount 132 results in a (−3) score each month but falling within the nutrient amount 132 range for those two nutrients affords (+1) score for each month; the target amount for the preceding month may dictate the score change for each subsequent month. In such a case, a machine-learning model may derive an algorithm which dictates the amount to increase/decrease body degradation score 148 for that particular degradation category 120 according to the nutrient amounts 132. In this case, the machine-learning model is trained to identify the relationship between nutrient amounts 132 and effect on degradation reduction to derive an equation that relates scoring criteria. The score is then calculated using the model and nutrition data as an input. Consumption by the user may include amounts and identities of nutrition elements 128. In this way, system 100 may calculate a body degradation score 148 as a function of a user's participation in body degradation reduction program 140, where body degradation score 148 is updated with each nutrition element 128 consumed by user.

Continuing in reference to FIG. 1, generating body degradation score 148 may include receiving nutritional input from user. "Nutritional input," as used in this disclosure, is an amount of a nutrient consumed by a user. Nutritional input may be received and/or calculated, for instance and without limitation, as described in Ser. No. 16/911,994, filed Jun. 25, 2020, titled "METHODS AND SYSTEMS FOR ADDITIVE MANUFACTURING OF NUTRITIONAL SUPPLEMENT SERVINGS," the entirety of which is incorporated herein by reference. System 100 may receive nutritional input from a user. Nutritional input, for instance and without limitation, may include food items that have associated nutrition facts, wherein computing device 104 may calculate, weight, or otherwise modify, the nutritional input from the user, such as with a weighting factor. This results in accurate, per-user nutritional input. That nutritional input may be used to determine the amount of target nutrient amounts 132 summarized in the body degradation reduction program 140 the user is consuming. Adherence to body degradation reduction program 140 may be determined from nutritional input, and the body degradation rates may be determined from the adherence to the degradation reduction program 140. Nutritional input of a user may include a designation of any nutrition elements 128 user may have consumed, such as via the user device and graphical user interface. Nutritional elements 120 may have nutrient amounts 132 associated therewith, which may be applied to a user's current body degradation profile 112, degradation category 120, and the like, representing an update to the data as the user consumes nutrition elements 128. Applying the nutrient amounts 132 may include calculating a difference in body degradation score 148. Applying the nutrient amounts 132 may include calculating a change in degradation risk, rates, or incidence of symptoms as a function of achieving nutrient amounts 132.

Figure 2:
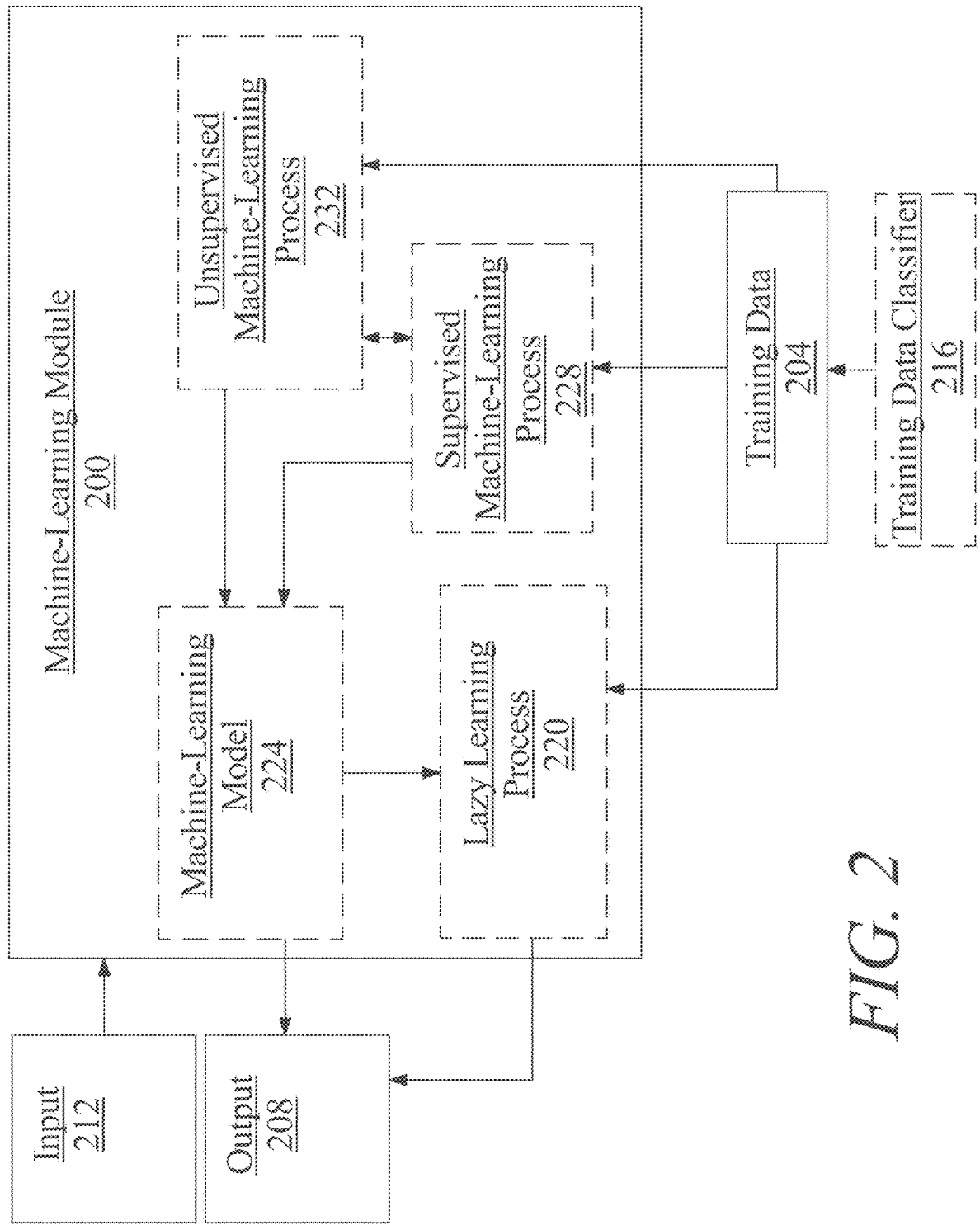
FIG. 2 is a block diagram illustrating a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a subject and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail herein. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail herein; such models may include without limitation a training data classifier 216. Training data classifier 216 may include a "classifier," which as used in this disclosure is a machine-learning model as defined herein, such as a mathematical model, neural net, or program generated by a machine learning algorithm known as a "classification algorithm," as described in further detail herein, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements that characterizes a sub-population, such as a subset of degradation markers 108 (such as gene expression patterns as it relates to body degradation profile 112) and/or other analyzed items and/or phenomena for which a subset of training data may be selected.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of predictions may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements, such as classifying degradation marker 108 elements to body degradation profile 112 elements and assigning a value as a function of some ranking association between elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail herein.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. A machine-learning model may be used to derive numerical scales for providing numerical values to body degradation profile 112 and/or body degradation score 148, and the like, as described above, to "learn" the upper and lower limits to the numerical scale, the increments to providing scoring, and the criteria for increasing and decreasing elements encompassed in the body degradation profile 112 and/or body degradation score 148, and the like A machine-learning model may be used to "learn" which elements of degradation markers 108 have what effect on body degradation profile 112, and which elements of body degradation profile 112 are affected by particular nutrition elements 128 and the magnitude of effect, and the like The magnitude of the effect may be enumerated and provided as part of system 100, where nutrition elements 128 are communicated to user for their degradation reduction properties.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a body degradation profile 112 (potentially classified into degradation categories 124), as described above as inputs, nutrition element 128 outputs, and a ranking function representing a desired form of relationship to be detected between inputs and outputs; ranking function may, for instance, seek to maximize the probability that a given input (such as nutrient amounts 132) and/or combination of inputs is associated with a given output (body degradation reduction program 140 that incorporate nutrient elements 120 to achieve nutrient amounts 132 that are 'best' for degradation category 120) to minimize the probability that a given input is not associated with a given output, for instance finding the most suitable times to consume meals, and what the meals should be, and the like. Ranking function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon the benefit of reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning process 232. An unsupervised machine-learning process 232, as used herein, is a process that derives inferences in datasets without regard to labels; as a result, an unsupervised machine-learning process 232 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 204.

Figure 3:
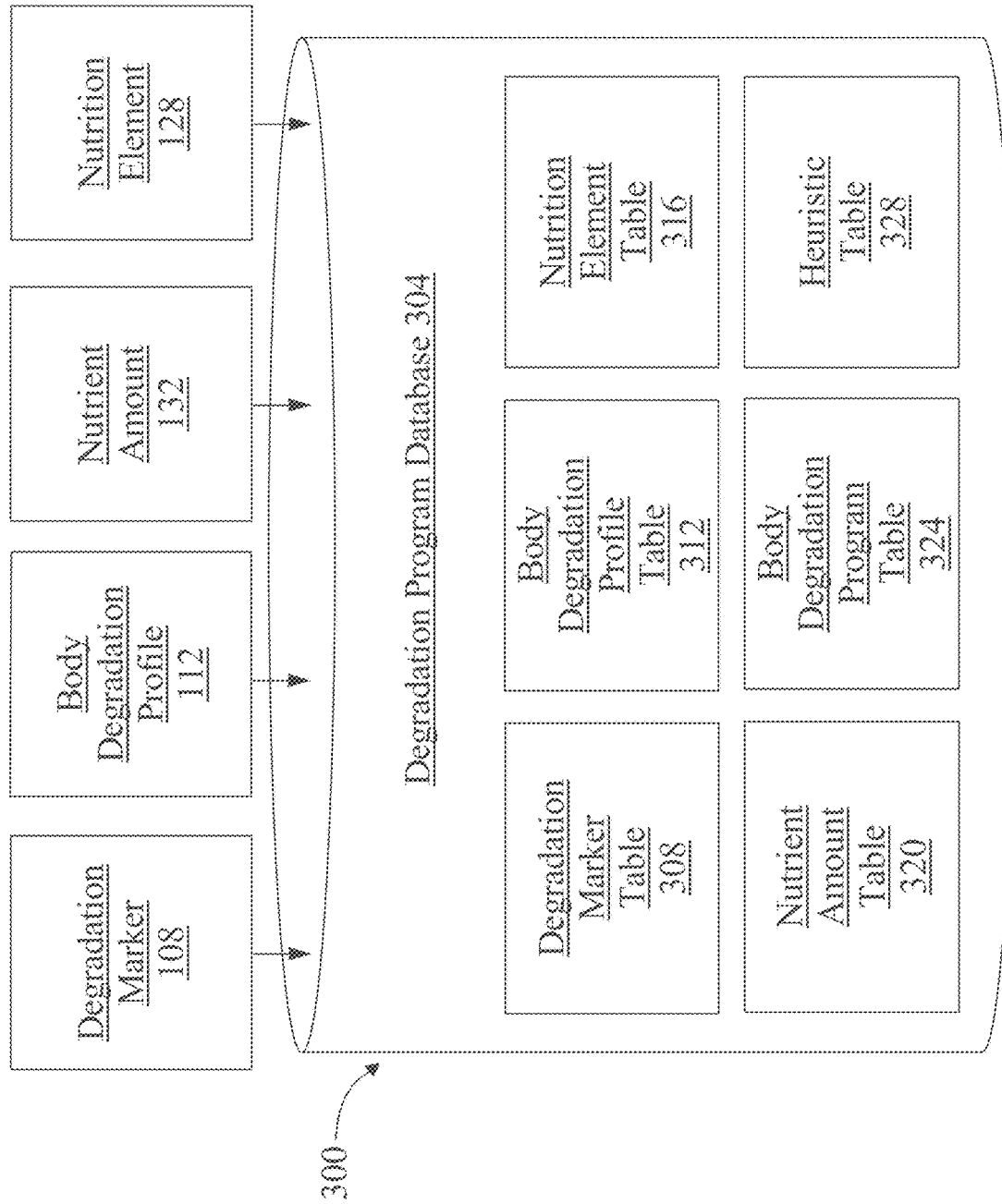
FIG. 3 is a block diagram of a degradation program database.

Referring now to FIG. 3, a non-limiting exemplary embodiment 300 of a degradation program database 304 is illustrated. Degradation marker(s) 108 from a plurality of users, for instance for generating a training data classifier 216, may be stored and/or retrieved in degradation program database 304. Degradation marker(s) 108 data from a plurality of users for generating training data 204 may also be stored and/or retrieved from a degradation program database 304. Computing device 104 may receive, store, and/or retrieve training data 204, wearable device data, physiological sensor data, biological extraction data, and the like, from degradation program database 304. Computing device 104 may store and/or retrieve nutrient machine-learning model 116, degradation classifier 124, among other determinations, I/O data, models, and the like, from degradation program database 304.

Continuing in reference to FIG. 3, degradation program database 304 may be implemented, without limitation, as a relational database, a key-value retrieval database such as a NOSQL database, or any other format or structure for use as a database that a person skilled in the art would recognize as suitable upon review of the entirety of this disclosure. Degradation program database 304 may alternatively or additionally be implemented using a distributed data storage protocol and/or data structure, such as a distributed hash table and the like. Degradation program database 304 may include a plurality of data entries and/or records, as described above. Data entries in a degradation program database 304 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 3, degradation program database 304 may include, without limitation, degradation marker table 308, body degradation profile table 312, nutrition element table 316, nutrient amount table 320, body degradation program database 324, and/or heuristic table 328. Determinations by a machine-learning process, machine-learning model, ranking function, and/or classifier, may also be stored and/or retrieved from the degradation program database 304. As a non-limiting example, degradation program database 304 may organize data according to one or more instruction tables. One or more degradation program database 304 tables may be linked to one another by, for instance in a non-limiting example, common column values.

For instance, a common column between two tables of degradation program database 304 may include an identifier of a submission, such as a form entry, textual submission, accessory device tokens, local access addresses, metrics, and the like, for instance as defined herein; as a result, a search by a computing device 104 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 3, in a non-limiting embodiment, one or more tables of a degradation program database 304 may include, as a non-limiting example, a degradation marker table 308, which may include categorized identifying data, as described above, including degradation marker 108 data such as genetic data, epigenetic data, microbiome data, physiological data, biological extraction data, and the like. Degradation marker table 308 may include degradation marker 108 categories according to gene expression patterns, SNPs, mutations, enzyme specific activity and concentration, phosphorylation data, proteasomal degradation data, data concerning metabolism of nutrition elements 128, pharmacokinetics, nutrient absorption, and the like, and may include linked tables to mathematical expressions that describe the impact of each degradation marker 108 datum on body degradation profile 112, for instance threshold values for gene expression, and the like, as it relates to degradation parameters, rates, degradation category 120, and the like. One or more tables may include body degradation profile table 312, which may include data regarding degradation marker 108, thresholds, scores, metrics, values, categorizations, and the like, that system 100 may use to calculate, derive, filter, retrieve and/or store current degradation levels, degradation types, symptom-degradation relationships, and the like. One or more tables may include nutrition element table 316, which may include data on nutrition elements 128 for instance classified to degradation category 120, classified to data from alike subjects with similar degradation marker 108, body degradation profile 112, and the like, that system 100 may use to calculate, derive, filter, retrieve and/or store nutrition elements 128. One or more tables may include nutrient amount table 320, which may include functions, model, equations, algorithms, and the like, using to calculate or derive nutrient amounts 132 relating to body degradation profile 112 and/or degradation category 120, may include nutrient amounts 132 organized by nutrient, nutrient classification, age, sex, degradation severity, and the like. One of more tables may include a body degradation program database 324, which may include nutrition element 128 identifiers, serving sizes, times associated with nutrition elements 128 regarding times to eat, identifiers of meals, recipes, ingredients, schedules, diet types, and the like. One or more tables may include, without limitation, a heuristic table 328, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Referring now to FIGS. 4A and 4B, a non-limiting exemplary embodiment 400 of a body degradation profile 112 is illustrated. Body degradation profile 112 may include a variety of degradation marker 108 categories, for instance 22 distinct categories, as shown in FIGS. 4A and 4B. Each degradation marker 108 may be assigned a value, such as an arbitrary value, where some degradation markers 108, such as those shaded in light grey, may relate to absolute scales from [0, x], where x is a maximal value and the range of values for the degradation marker 108 cannot be below a 'zero amount'. Some degradation markers 108, such as those shaded in dark grey, may relate to gene expression levels, wherein, the degradation marker 108 is enumerated as a 'box plot' that illustrates the range of expression in a population of users organized according to, for instance tissue type. In such an example, the dashed line may relate to a 'normal threshold' above which is elevated gene expression, below which is decreased expression level. Each degradation marker 108 may have associated with it a numerical score, or some other identifying mathematical value that computing device 104 may assign. Persons skilled in the art, upon the benefit of this disclosure in its entirety, may appreciate that for each user, any number of degradation markers 108 may be enumerated and assigned a value according to body degradation profile machine-learning model 116. Body degradation profile 112 may be graphed, or otherwise displayed, according to the enumeration by body degradation profile machine-learning model 116. Each bar of the bar graph, or combinations of bar graph categories, may instruct a classification of a user's body degradation profile 112 to a degradation category 120.

Still referring now to FIGS. 4A and 4B, in non-limiting exemplary illustrations body degradation profile 112 may be classified to a degradation category 120. Some and/or all of the degradation markers 108 summarized in body degradation profile 112 may be used to classify an individual to a particular degradation category 120. For instance, as shown in FIG. 4B, ten of the 22 degradation marker 108 categories may be used to classify body degradation profile 112 to one or more degradation categories 124. Alternatively or additionally, body degradation profile machine-learning model 116 may be trained to assign degradation marker 108 to a degradation category 120, wherein computing device 104 may know the identity of degradation category 120 according to which degradation category 120 has the most identifying data points. Alternatively or additionally, degradation classifier 124 may be trained to assign user to a degradation category 120 according to patterns observed in degradation markers 108, for instance according to data from a subset of users.

Figure 5:
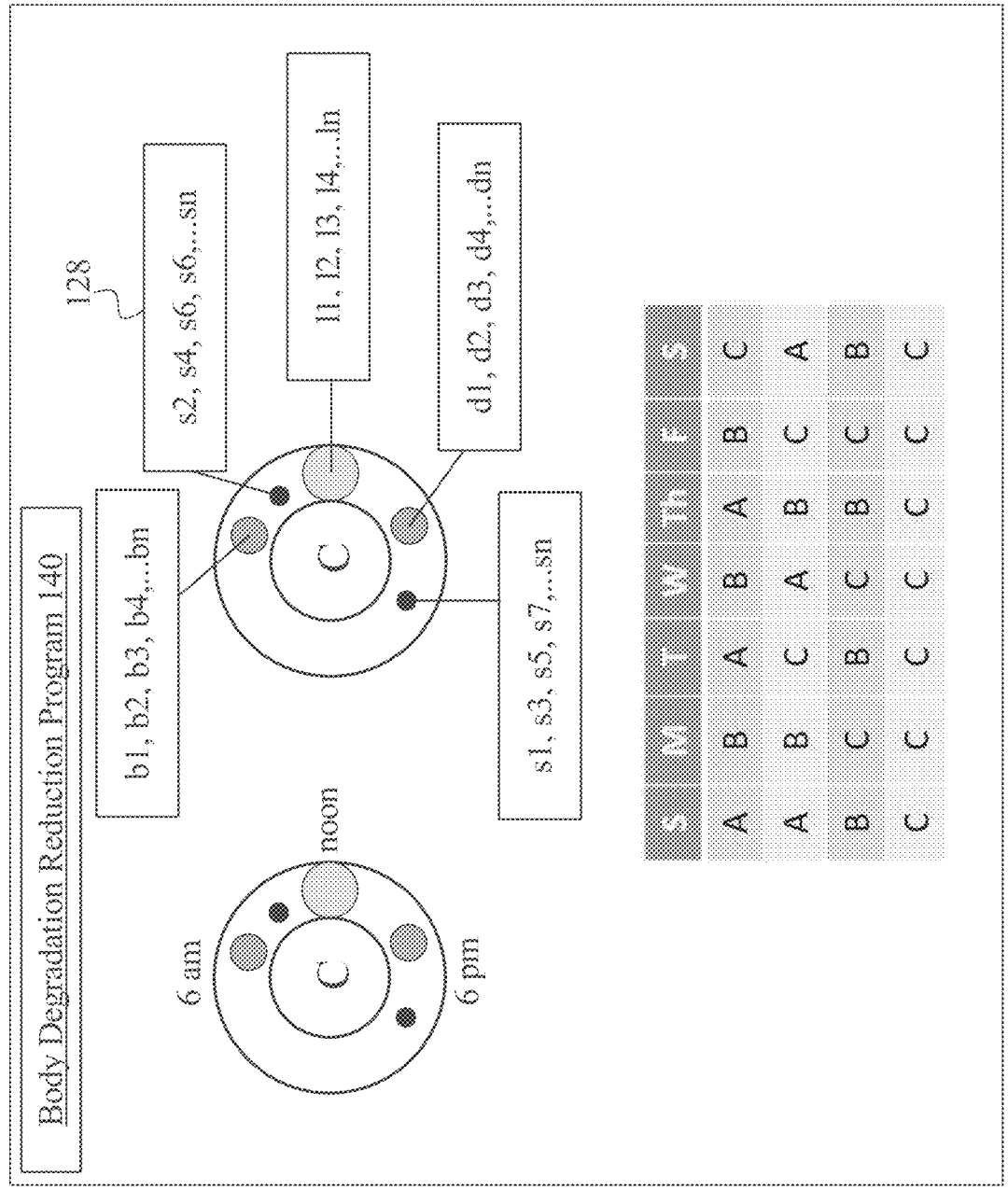
FIG. 5 is a diagrammatic representation of a body degradation reduction program.

Referring now to FIG. 5, a non-limiting exemplary embodiment 500 of a body degradation reduction program 140 is illustrated. Body degradation reduction program 140 may include a schedule for arranging nutrition elements 128, according to for instance a 24-hour timetable, as designated on the left, where consumption is planned along a user's typical day-night cycle, beginning at ~6 am until just after 6 pm. Nutrition element 128 may include breakfast (denoted as mid-sized dark grey circle), which may correspond to a file of breakfast-related plurality of nutrition elements 128 (denoted b1, b2, b3, b4 . . . bn, to the nth breakfast item). Nutrition element 128 may include snacks eaten throughout the day to, for instance achieve nutrient amounts 132 missing from meals (denoted as small black circles), which may correspond to a file of snacking-related plurality of nutrition elements 128 (denoted s1, s2, s3, s4 . . . sn, to the nth snacking item). Nutrition element 128 may include dinner (denoted as large-sized light grey circle), which may correspond to a file of dinner-related plurality of nutrition elements 128 (denoted d1, d2, d3, d4 . . . dn, to the nth dinner item). Body degradation reduction program 140 may include a variety of diets, as denoted in the monthly schedule at the bottom, Sunday through Saturday. Body degradation reduction program 140 'C.' is shown, which may be an idealistic goal for user to achieve by the end of the month, where nourishment plan 'A' and 'B' are intermediate plans intended to wean user to the 'ideal' plan. Nutrition elements 128 classified by 'meal type' may be further modified by 'A' and 'B' according to user preferences 148 collected by computing device 104 throughout the process. Circle sizes, denoting nutrition element 128 classes may relate to portion sizes, which are graphed along the circle corresponding to the times they are expected to be consumed. User may indicate which nutrition element 128 from each category was consumed, and when it was consumed, to arrive at body degradation score 148.

Figure 6:
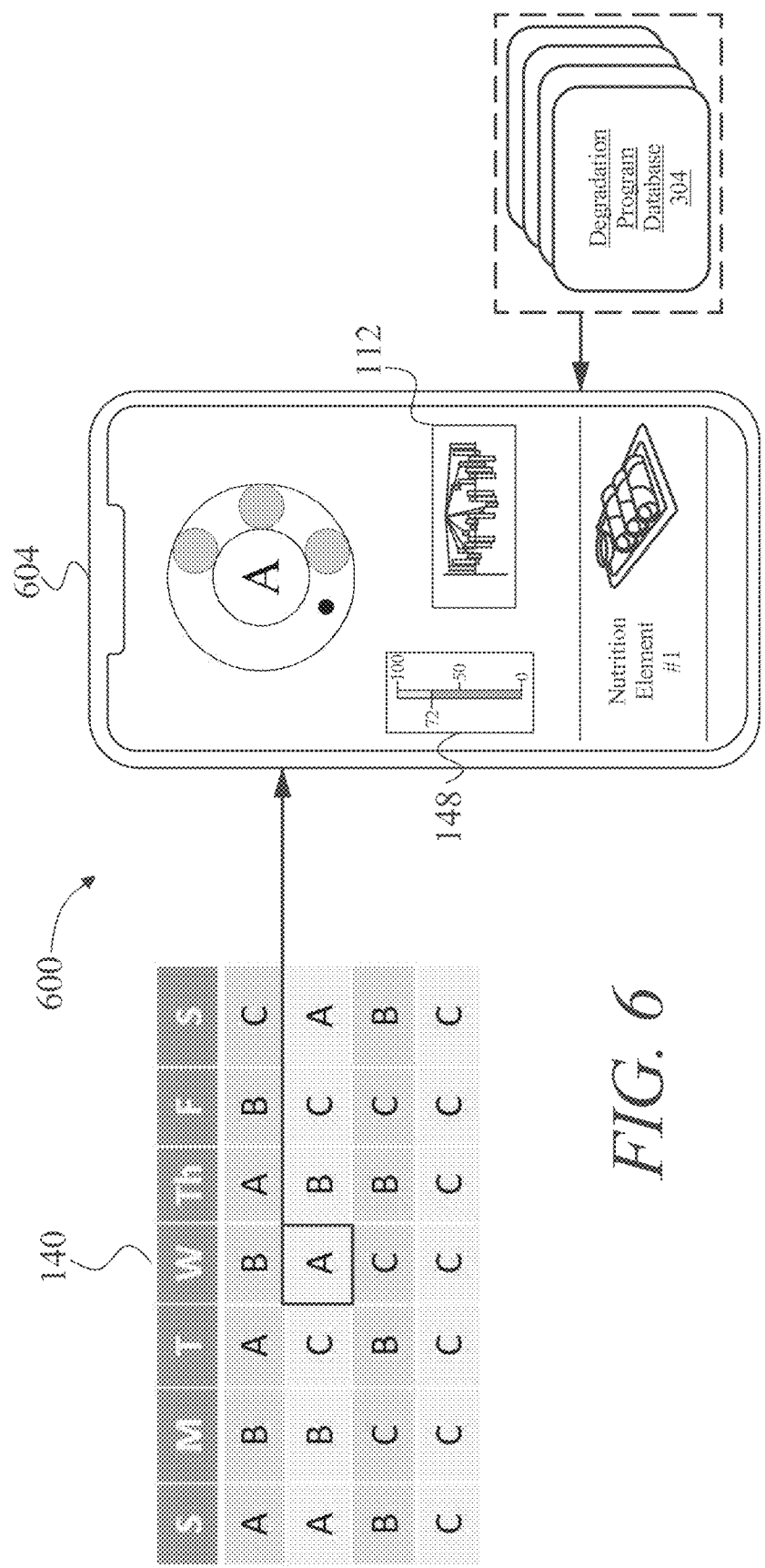
FIG. 6 is a diagrammatic representation of a user device.

Referring now to FIG. 6, a non-limiting exemplary embodiment 600 of a user device 604 is illustrated. User device 604 may include computing device 104, a "smartphone," cellular mobile phone, desktop computer, laptop, tablet computer, internet-of-things (IOT) device, wearable device, among other devices. User device 604 may include any device that is capable for communicating with computing device 104, degradation program database 304, or able to receive, transmit, and/or display, via a graphical user interface, body degradation profile 112, nutrition element 128, body degradation reduction program 140, body degradation score 148, among other outputs from system 100. User device 604 may provide a body degradation profile 112, for instance as a collection of metrics determined from degradation marker 108 data. User device 604 may provide degradation category 120 that was determined as a function of degradation classifier 124 and body degradation profile 112. User device 604 may provide data concerning nutrient amounts 132, including the levels of specific nutrients, nutrient ranges, nutrients to avoid, and the like. User device 604 may link timing of foods to preemptive ordering interface for ordering a nutrition element 128, for instance and without limitation, through a designated mobile application, mapping tool or application, and the like, and a radial search method about a user's current location as described in U.S. Nonprovisional application Ser. No. 17/087,745, filed Nov. 3, 2020, titled "A METHOD FOR AND SYSTEM FOR PREDICTING ALIMENTARY ELEMENT ORDERING BASED ON BIOLOGICAL EXTRACTION," the entirety of which is incorporated herein by reference. User device 604 may display nutrient elements 120 as a function of location, for instance and without limitation, as described in User device 604 may link nourishment consumption program 120 to a scheduling application, such as a 'calendar' feature on user device, which may set audio-visual notifications, timers, alarms, and the like.

Figure 7:
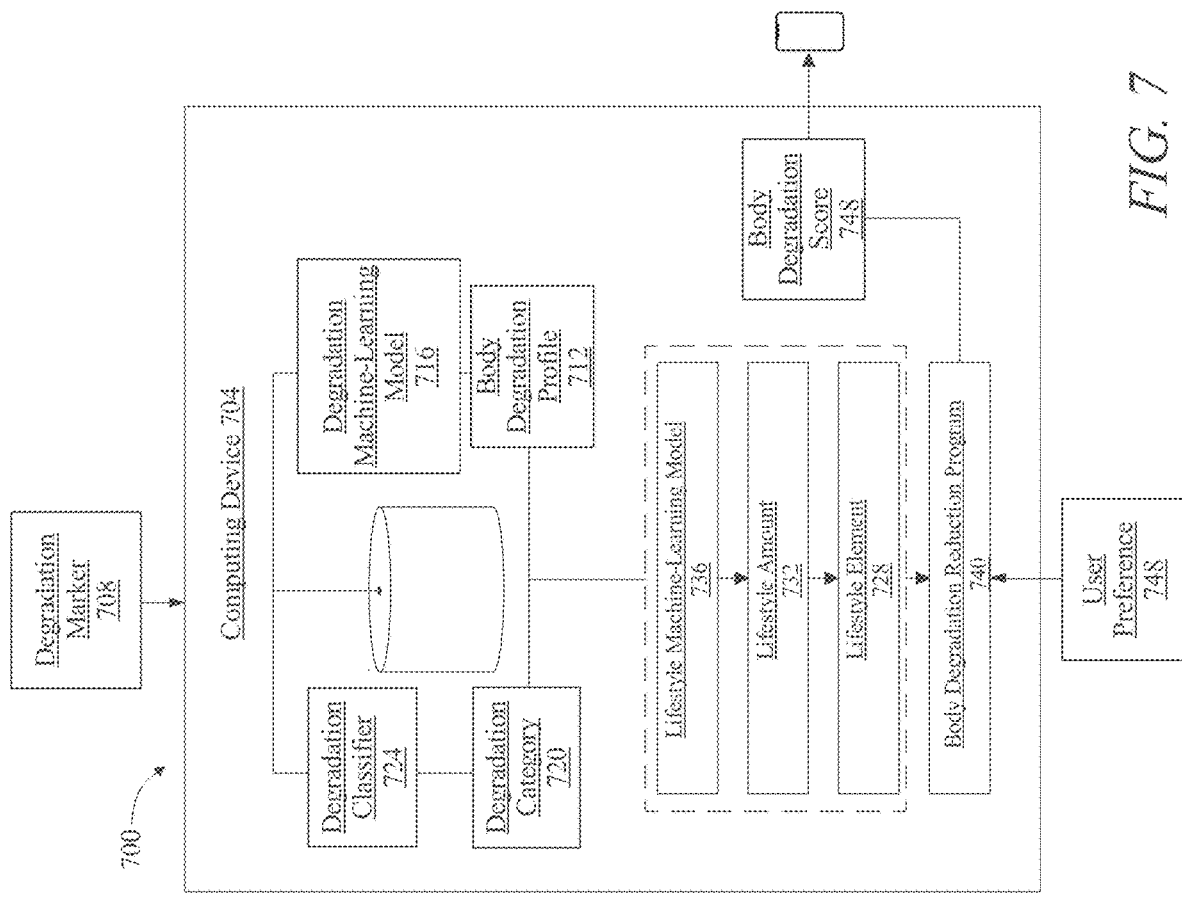
FIG. 7 is a block diagram illustrating a system for generating a body degradation reduction program.

Referring now to FIG. 7, an exemplary embodiment of a system 700 for generating a body reduction program 740 is illustrated. System 700 includes a computing device 704. Computing device 704 may include any computing device as described in this disclosure, including without limitation a microcontroller, microprocessor, digital signal processor (DSP) and/or system on a chip (SoC) as described in this disclosure. Computing device 704 may be designed and/or configured to perform any method, method step, or sequence of method steps in any embodiment described in this disclosure, in any order and with any degree of repetition. For instance, computing device 704 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 704 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 7, computing device 704 may be configured to receive a degradation marker 708 related to a user. Degradation marker 708 may include data indicative of biological degradation over the lifetime of the user. Degradation marker 708 may include biological molecules existing within a normal cell, a stressed cell, disease state cell, and/or a specific response of the body indicative of deterioration and/or aging. Receiving the degradation marker 708 may include receiving a result of one or more tests relating the user. Degradation marker 708 may include degradation marker 108 as described in FIG. 1. In some embodiments, degradation marker 708 may be organized into data sets and stored and/or retrieved by computing device 704, without limitation, as a relational database, a key-value retrieval database such as a NOSQL database, or any other format or structure for use as a database that a person skilled in the art would recognize as suitable upon review of the entirety of this disclosure.

Continuing in reference to FIG. 7, computing device 704 may be configured to retrieve a body degradation profile 712 related to the user. Body degradation profile 712 may include at least a degradation rate of biological degradation. The degradation level may include a relative level of physiological integrity compared to theoretical level of physiological integrity according to what is scientifically achievable for an individual. Body degradation profile 712 may include at least a degradation rate which may be an instantaneous rate or a rate that is over a variable range of time. Body degradation profile 712 may include biological degradation such as physiological deterioration of, for instance and without limitation, vision, hearing, cardiovascular endurance, maintenance of lean body mass, bone mineral density, short-term memory, mental plasticity, neurodegeneration, telomere length, and the like. Body degradation profile 712 may include the body degradation profile as described in FIG. 1.

Continuing in reference to FIG. 7, retrieving body degradation profile 712 may include receiving data via a graphical user interface. Graphical user interface may accept input, wherein input may include an interaction (such as a questionnaire) with a user device. A user device, as described in further detail below, may include computing device 704, a "smartphone," cellular mobile phone, desktop computer, laptop, tablet computer, internet-of-things (JOT) device, wearable device, among other devices. User device may include any device that is capable for communicating with computing device 704, database, or able to receive data, retrieve data, store data, and/or transmit data, for instance via a data network technology such as 3G, 4G/LTE, 5G, Wi-Fi (IEEE 802.11 family standards), and the like. User device may include devices that communicate using other mobile communication technologies, or any combination thereof, for short-range wireless communication (for instance, using Bluetooth and/or Bluetooth LE standards, AirDrop, Wi-Fi, NFC, and the like), and the like.

Still referring to FIG. 7, retrieving the body degradation profile 712 related to the user may performed using a training degradation machine-learning model 716. This may include, without limitation, training degradation machine-learning model 716 using training data. Training data, which may be implemented in any manner described in this disclosure, may include a plurality of data entries wherein each entry may correlate degradation markers to biological degradation data. Computing device 704 may train machine-learning model 716 using training data and any machine-learning algorithm or combination thereof as described in this disclosure. Computing device 704 may generate body degradation profile 712 as a function of degradation machine-learning model 716 and at least a degradation marker 708. Degradation machine-learning model 716 may include any machine-learning process, algorithm, and/or model as performed by machine-learning module, described in further detail below. Generating body degradation profile 712 as a function of training data and a machine-learning model may be performed, without limitation, as described in reference to FIG. 1

Continuing in reference to FIG. 7, training data for degradation machine-learning model 716 may include degradation markers 712 organized into training data sets, as described above, including results from biological extraction samples, health state questionnaires regarding symptomology, medical histories, physician assessments, lab work, and the like. Training data may be retrieved from a database, as described in further detail below. Body degradation profile 712 training data may originate from the subject, for instance via a questionnaire and a user interface with computing device 704, for user to provide medical history data and/or symptoms. Receiving body degradation profile training data may include receiving whole genome sequencing, gene expression patterns, and the like, for instance as provided by a genomic sequencing entity, hospital, database, the Internet, and the like. Body degradation profile 712 training data may include raw data values recorded and transmitted to computing device 704 via a wearable device such as a pedometer, gyrometer, accelerometer, motion tracking device, bioimpedance device, ECG/EKG/EEG monitor, physiological sensors, blood pressure monitor, blood sugar and volatile organic compound (VOC) monitor, and the like. Body degradation profile 712 training data may originate from an individual other than user, including for instance a physician, lab technician, nurse, dietician, strength coach, psychologist, and the like. It is important to note that training data for machine-learning processes, algorithms, and/or models used within system 700 herein may likewise originate from any source described for body degradation profile 712 training data.

Continuing in reference to FIG. 7, body degradation profile machine-learning model 716 may include any machine-learning algorithm such as K-nearest neighbors algorithm, a lazy naïve Bayes algorithm, among other algorithms, machine-learning process such as supervised machine-learning, unsupervised machine-learning, or method such as neural nets, deep learning, and the like. Body degradation profile machine-learning model 716 may be trained to derive an equation, function, series of equations, or any mathematical operation, relationship, or heuristic, that may automatedly accept an input, such as degradation marker(s) 708, and correlate, classify, or otherwise calculate an output, such as degradation parameter(s). Body degradation profile machine-learning model 716 may include individual functions, derived for unique relationships observed from the training data for each degradation marker 708. In non-limiting illustrative examples, the parameters involved in a variety of physiological tests, as identified above, may be retrieved from a database, such as a repository of peer-reviewed research (e.g. National Center for Biotechnology Information as part of the United States National Library of Medicine), and the degradation profile machine-learning model 716 may derive an algorithm which may determine an average and statistical evaluation (mean±S.D.) calculated from the data, across which the user's parameters may be compared. In such an example, degradation profile machine-learning model 716 may derive an algorithm according to the data used to derive the average and statistical evaluation changes as a function of the subset of data to which the user is to be compared, for instance and without limitation, based on age, fitness level, nutrition deficiency, symptomology, past diagnoses, and the like.

Continuing in reference to FIG. 7, computing device 704 may be configured to assign body degradation profile 712 to a degradation category 720. Degradation category 720 may include a designation of a degradation type. Degradation category 720 may include tissue and/or organ such as "kidney degradation", "liver degradation", "peripheral nervous system degradation", and the like. Degradation category 720 may include a designation regarding a degradation type that may not involve a particular tissue such as "vision degradation", "hearing degradation", "short term memory loss", and the like. Degradation category 720 may include pathological, histological, and/or clinical classification identifiers such as "telomeric length loss of >35 bp/year", "Mini-Mental State Exam (MMSE) score range of 20-24", "myelin sheath thinning", and the like. Degradation category 720 may include identifiers associated with disorders, conditions, symptoms, and the like, which may correspond with categorization. Degradation category 720 may include a predictive degradative classification, where a user such as a healthy young adult, does not harbor degradation marker(s) 708 indicative of obvious current degradation but may include data that indicates a degradation category 720 with which they may be most closely categorized to. For instance, a family history of vision loss as a function of aging due to a combination of epigenetic elements, lifestyle factors, and long-term nutritional impacts, may classify an individual in "vision degradation" degradation category 720, despite not currently exhibiting lessened vision acuity, astigmatism, or other loss of vision integrity. Body degradation profile 712 may have associated with it an identifier, such as a label, that corresponds to a degradation category 720. Degradation category 720 may be stored and/or retrieved from a database.

Continuing in reference to FIG. 7, assigning the body degradation profile 712 to a degradation category 720 may include training a degradation classifier 724 using a degradation classification machine-learning process and training data which includes a plurality of data entries of body degradation profile data from subsets of categorized users. Degradation classifier 724 may be generated by a degradation classification machine-learning process 728, which may include any machine-learning algorithm, process, and/or model described herein performed by a machine-learning module, as described in further detail below. Degradation classification machine-learning process 728 may generate degradation classifier 724 using training data. A classifier may include a machine-learning model, such as a mathematical model, neural net, or program generated by a machine learning algorithm known as a "classification algorithm". Degradation classifier 724 may sort inputs, such as body degradation profile 712, into categories or bins of data, such as classifying the data into degradation category 720, outputting the bins of data and/or labels associated therewith.

Continuing in reference to FIG. 7, training data for degradation classifier 724 may include a set of degradation markers 708 as it relates to classes of degradation types, organ and/or tissue types, ability types, and the like. For instance and without limitation, training data may include ranges of degradation markers 708 as they correlate to various degrees of vision loss, hearing integrity, maintaining musculoskeletal integrity, and the like. Such training data may include degradation markers 708 as it relates to degradation category 720 for subsets of a plurality of users, segmented according to user characteristics such as smoking, exercise, diet, age, sex, alcohol consumption, ethnicity, and the like. Training data may be used by classification machine-learning process to train a classifier to derive relationships present in the data that may result in a machine-learning model that automatedly classifies a user to a degradation category 720 as a function of the data present in their body degradation profile 712. Training data may originate from any source described herein, for instance retrieved from a database, retrieved via a web browser and the Internet, peer-reviewed research repository, clinical data, user input data, wearable device, physiological sensor, medical history data, and the like.

Continuing in reference to FIG. 7, degradation classifier 724 may be configured to output at least a datum that labels or otherwise identifies a set of data that are clustered together, found to be close, relate to one another via a metric, scoring, probability, and the like, as described below. Machine-learning module, as described in further detail below, may generate a classifier using a classification algorithm, defined as a process whereby computing device and/or any module and/or component operating thereon derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, a body degradation profile 712 training data classifier may classify elements of training data to elements that characterizes a sub-population, including subset of degradation marker 708 such as gene expression patterns and epigenetic markers as it relates to a variety of degradation types and/or other analyzed items and/or phenomena for which a subset of training data may be selected.

Continuing in reference to FIG. 7, assigning the body degradation profile 712 to a degradation category 720 may include classifying the body degradation profile 712 to a degradation category 720 using the degradation classifier 724. Classification using degradation classifier 724 may include identifying which set of categories (degradation category 720) an observation (body degradation profile 712) belongs. Classification may include clustering based on pattern recognition, wherein the presence of degradation markers 708, such as genetic indicators, symptoms, and the like, identified in body degradation profile 712 relate to a particular degradation category 720. Such classification methods may include binary classification, where the body degradation profile 712 is simply matched to each existing degradation category 720 and sorted into a category based on a "yes"/"no" match. Classification done in such a manner may include weighting, scoring, or otherwise assigning a numerical value to elements in body degradation profile 712 as it relates to each body degradation type and assign a user to a degradation category 720 that results in the highest score. Such a score may represent a "likelihood", probability, or other statistical evaluation that relates to the classification into degradation category 720.

Continuing in reference to FIG. 7, computing device 704 may assign the degradation category 720 as a function of the classifying. Classifying the body degradation profile 712 (input) to a degradation category 720 (output) may include assigning the degradation category 720 as a function of the degradation classifier 724 generated by the degradation classification machine-learning process 728. Training data for degradation classifier 724 may include sets of degradation parameters and/or degradation markers 708, as described above, correlated to degradation category according to trends observed in the data for subsets of users. Such training data may be used to learn how to categorize a user's body degradation profile 712 to degradation categories depending on trends in the data. In this way, degradation classifier 724 may also generate new degradation categories depending on how well a user may "fit" within a particular classification.

Continuing in reference to FIG. 7, computing device 704 may be configured to identify, using the body degradation profile 712, a plurality of lifestyle elements 728 for a user. A "lifestyle element," as used in this disclosure, is an activity a user may engage in that may impact a user's overall health. A "lifestyle," as used in this disclosure, is a plurality of habits and/or activities a user engages with on a daily, weekly, and/or monthly basis. Lifestyle element 728 may include, but is not limited to, eating, exercising, meditating, sleeping, socializing, stretching, praying, reading, brain teasers, coordination training, cognitive training, and the like. Lifestyle element 728 may be "personalized" in that lifestyle elements may be curated in a guided manner according to body degradation profile 712, degradation markers 708, user preferences, and the like. In some embodiments, identifying a plurality of lifestyle elements 728 may include generating a plurality of lifestyle elements that aid in reduction of body degradation as a function of the degradation category 720. Generating a plurality of lifestyle elements may include querying for lifestyle elements that are correlated to degradation category 720, for instance using a web browser and the Internet using the degradation category 720 as a search guide. In some embodiments, identifying a plurality of lifestyle elements 728 may include determining a respective effect of each lifestyle element amount of the plurality of lifestyle elements 728 on body degradation profile 712. An "effect of a lifestyle element," as used in this disclosure, is a change, consequence, and/or result in at least a degradation marker 708, body degradation profile 712, degradation category 720, and/or rate of biological degradation in a user due to engagement of an amount of a lifestyle element. An effect of a lifestyle element may be "no effect", "negligible effect", and/or "no calculated effect". Determining an effect of a lifestyle element may include determining how a degradation marker 708 may change, such as an increase/decrease according to a particular amount of a lifestyle element. For instance and without limitation, such a determination may include calculating the effect of chronic, sustained lifestyle element amounts in a lifestyle for weeks and/or months on epigenetic factors, blood serum levels of biomarkers, and the like. An effect may include changes in current rates and/or risk of degradation and/or future rates and/or risks of degradation.

Continuing in reference to FIG. 7, determining a respective effect of each lifestyle element amount of the plurality of lifestyle elements may include retrieving the effects of the lifestyle element amount on the body degradation profile as a function of degradation marker 708. Computing device 704 may search for a lifestyle element effect using each degradation marker 708, and/or combination thereof, to locate and retrieve effects correlated to lifestyle elements targeting a degradation marker 708. Retrieving an effect of a lifestyle element may include retrieving a hypothesis about the outcome for a user after engaging in an amount and/or amount of a combination of lifestyle elements. Such a hypothesis may include an equation, function, among other mathematical forms, for instance derived from empirical relationships between a lifestyle element and the physiological integrity of an organ, biological system, and the like. Retrieving an effect may include retrieving from a database, a research repository, or the like. Retrieving an effect may include, for instance, searching using the body degradation profile 712, a web browser, and the Internet, for a plurality of effects that lifestyle elements may have. Retrieving an effect may include searching using the degradation category 720 for an effect of a lifestyle element on the type of degradation. In some embodiments, retrieving an effect may include calculating at least an effect, for instance by deriving a function from training data using a machine-learning algorithm.

Continuing in reference to FIG. 7, in non-limiting illustrative examples, determining an effect of a lifestyle element may include calculating if a change in degradation category 720 may arise from adding and/or removing a lifestyle element from a user's habits. For instance and without limitation, changing a degradation category 720 from "elevated muscle atrophy" to "reduced muscle atrophy" with increasing exercise by introducing lifestyle elements 728 a user may not currently engage in, such as strength training, calisthenics, aerobic exercise, and the like. Calculating an effect of a lifestyle element may include a mathematical operation, such as subtraction, addition, and the like. Calculating an effect of a lifestyle element may include retrieving an empirical equation that describes relationships between a lifestyle element and degradation marker 708, test results, degradation parameter, and the like. Calculating an effect of a lifestyle element may include deriving an algorithm, function, or the like, for instance using a machine-learning process and/or model. Calculating such an effect using machine-learning may include training data that includes a plurality of lifestyle elements as it relates to effects on degradation categories 724, degradation markers 708, and the like.

Continuing in reference to FIG. 7, determining a respective effect of each lifestyle element amount of the plurality of lifestyle elements may include generating a machine-learning model. Training data may include lifestyle element amounts correlated to their effect on the human body. For instance and without limitation, meditation may be correlated to reduced stress levels, reduced cortisol levels, increased concentration levels, and the like. Such training data may originate from a database, research repository, clinical data, physician, plurality of users, or any other source described herein. Computing device 704 may generate a machine-learning model with such training data to derive an equation and/or function which describes relationships observed in the training data. Computing device 704 may then automatedly derive a respective effect for each lifestyle element, wherein the effect may become increasingly defined by parameters relating to the type of degradation in the user. The effect may also be related to an equation wherein, the magnitude of effect may be determined for all amounts of the lifestyle element. In this way, a particular lifestyle element amount may be determined based on the magnitude of effect desired.

Continuing in reference to FIG. 7, identifying a plurality of lifestyle elements 728 may include calculating a plurality of lifestyle element amounts as a function of the respective effect of each of the plurality of lifestyle element amounts, wherein the plurality of lifestyle element amounts comprises a plurality of amounts intended to result in body degradation reduction corresponding to the degradation category 720. A "lifestyle element amount," as used in this disclosure, is a numerical value(s) relating to the amount of engagement with a lifestyle element. Lifestyle element amount 732 may include periods of time of engagement in activities such as meditating, exercising, stretching, eating, sleeping, cognitive training, and the like. In some embodiments, calculating the plurality of lifestyle element amounts 732 may include generating training data using the plurality of predicted effects of the plurality of lifestyle element amounts 732. Training data may include retrieving effects on degradation for lifestyle elements, as described above, and generating training data which includes lifestyle element amounts correlated to degradation category 720 the lifestyle element is intended to target. Training data may include lifestyle element identities correlated to particular body degradations, for instance stretching correlated to muscle and/or join range of motion degradation.

Continuing in reference to FIG. 7, calculating lifestyle element amounts 732 may include deriving a weighting factor to adjust, or otherwise re-calculate, an amount. Weighting factor may be determined by computing device 704, for instance, by querying for exercise amounts according to data inputs identified in the body degradation profile 712. For instance in non-limiting illustrative examples, if body degradation profile 712 indicates the presence of advanced telomere shortening as indicated from increase expression of stathmin-family genes, EF-1a, and p16, the biomarkers of telomeric dysfunction and DNA damage in cells. Telomere shortening is a natural process of the loss of chromosomal genetic material from the ends of chromosomal DNA which accumulates as an organism ages; telomere shortening in the genetic disorder, dyskeratosis congenita, is associated with an early onset of several age-associated disorders and reduced lifespan. Relationships may be found in lifestyle element amounts 732 relating to the slowing of telomere shortening, specifically in supplementing a lifestyle with specific activities such as running, weightlifting, cycling, walking, meditating, swimming, and stretching, whereas it may be inversely associated with watching TV. In some embodiments, computing device 704 may be configured to identify the plurality of lifestyle elements 728 as a function of the plurality of lifestyle element amounts 732. Identifying the plurality of lifestyle elements 728 may include retrieving nutrition elements that include at least a lifestyle element amount of the plurality of lifestyle element amounts 732. Computing device 704 may accept an input of at least a lifestyle element amount 732 and retrieve lifestyle elements 728 by searching a database for lifestyle elements according to the lifestyle element and lifestyle element amount. Computing device 704 may accept an input of lifestyle element amount 732 and may search using a web browser and the Internet for lifestyle elements 728 according to the lifestyle element and its amount.

Continuing in reference to FIG. 7, identifying the plurality of lifestyle elements 728 may include identifying the lifestyle elements 728 according to the degradation category 720. Identifying lifestyle element 728 according to degradation category 720 may include querying, for instance using a web browser and the Internet, for foods, supplements, bioactive ingredients, and the like, which are correlated with a particular degradation category 720. For instance and without limitation, computing device 704 may organize a search for activities intended for "musculoskeletal degradation", wherein an entire activity routine may be crafted around target lifestyle element amounts 732 and the categorization of the body degradation profile 712 to "musculoskeletal degradation". In such an example, lifestyle elements 728 are outputs generated from an input search criteria of "musculoskeletal degradation". The output elements become "personalized" as they are arranged into daily, weekly, monthly, and the like, individual activities and/or activity schedule according to a user's particular calculated lifestyle element amounts 732. The degradation category 720 may serve as a filtering step, wherein a search is guided by the body degradation profile 712 as it was classified to a degradation type. In some embodiments, identifying the plurality of lifestyle elements 728 may include generating combinations of located lifestyle elements as a function of fulfilling the plurality of lifestyle element amounts 732. Computing device 704 may identify the plurality of lifestyle elements 728 by using lifestyle element amount 724 as an input and generating combinations, lists, or other aggregates of lifestyle elements 728 necessary to achieve lifestyle element amount 724.

Continuing in reference to FIG. 7, computing device 704 may be configured to generate a body degradation reduction program 740 using the plurality of lifestyle elements 728. Body degradation reduction program 740 may include a frequency and a magnitude for reducing body degradation of a user revolving around the user's lifestyle. In some embodiments, body degradation reduction program 740 may include a collection of lifestyle element amounts 732 and lifestyle elements 728 for reducing body degradation of an individual. Body degradation reduction program 740 may be organized into a frequency (timing) and magnitude (intensity of activity) schedule. A frequency may include a number of engagement occurrences associated with a time course, such as daily, weekly, monthly, and the like, of which a lifestyle element is intended to be engaged with. Frequency may be determined as a function of the identified effect, wherein the frequency of engagement may be tailored to provide a sufficient minimal lifestyle element level over a time. A magnitude may include an intensity of an engagement of a lifestyle element as a function of the identified effect. Identifying the magnitude associated with a lifestyle element may include calculating a period of time and intensity of the lifestyle element as a function of the identified effect. Lifestyle body degradation reduction program 740 may include gathering, classifying, or otherwise categorizing lifestyle element amounts 732 and/or lifestyle elements 728 lists, which incorporates degradation-specific recommendations. For instance, lifestyle elements 728 may be scored with a numerical score scale that associates an activity with preventing degradation, benefit to degradative symptoms, and the like. Body degradation reduction program 740 may include selecting lifestyle elements 728 according to a threshold score, where items above the threshold are selected and arranged into meals. Threshold score may include a daily threshold, wherein lifestyle elements 728 are selected each day according to the threshold; and threshold may include a numerical value relating to degradation prevention, a calculated lifestyle element amount 732, among other outputs of system 700 described herein. Determining body degradation reduction program 740 may include machine-learning. For instance and without limitation, training a machine-learning model to identify a scoring rubric for building the body degradation reduction program 740 based on some criteria such as preventing future degradation, alleviating symptoms, among other criteria. Body degradation reduction program 740 may relate specific degradation category 720 to specific lifestyle elements of interest and provide lifestyle element 728 scheduling times and engagement intensities for each activity. Body degradation reduction program 740 may differ from one user to the next according to the magnitude of the disease outline (degradation category 720 and body degradation profile 712).

Continuing in reference to FIG. 7, generating the body degradation reduction may include receiving a user preference. A "user preference", as used in this disclosure, is a user input that designates a preference related to at least a lifestyle element 728. User preference 744 may include designations of lifestyle elements 728 to avoid and/or include such as particular exercises, meditation forms, cognitive training, reading and the like. User preference 744 may include indications of activity restrictions which may represent constraints on curating lifestyle elements 728. In this way, computing device 704 may accept an input of user preference 744 filter, sort, classify, or otherwise modify the data structure of lifestyle elements 728 and schedule the lifestyle elements 728 into lifestyle body degradation reduction program 740 in a custom, per-user manner. Computing device 704 may modify the plurality of lifestyle elements 728 as a function of the user preference 744, for instance by providing recipes with steps omitted, new steps added, or entirely new recipes altogether utilizing the same or different lifestyle elements 728. Computing device 704 may modify the plurality of lifestyle elements 728 as a function of the user preference 744 by generating a new file, based on the preference, and storing and/or retrieving the file from a database, as described in further detail below.

Continuing in reference to FIG. 7, generating the body degradation reduction program 740 may include generating an objective function with the at least a plurality of lifestyle elements 728 wherein the objection function outputs at least an ordering of a plurality of lifestyle elements according to constraints from the degradation category 720 and the user preference 744. An objective function may include performing a greedy algorithm process. For instance, computing device 704 may select combinations of lifestyle elements 728 so that values associated therewith are the best value for each category. For instance, in non-limiting illustrative example, optimization may determine the combination of the most efficacious 'engagement intensity', 'period of engagement', 'mediation form', 'strength training', among other categories to provide a combination that may include several locally optimal solutions but may or may not be globally optimal in combination. In some embodiments, an objective function may be formulated as a linear objective function, which computing device 704 may solve using a linear program, such as without limitation, a mixed-integer program. For instance, in non-limiting illustrative examples, a given constraint might be a metabolic disorder of a user, as indicated by user preference 744, and a linear program may use a linear objective function to calculate combinations, considering how these limitations effect combinations. In various embodiments, system 700 may determine a set of instructions towards addressing a subject's body degradation profile 712 that maximizes a total degradation prevention score subject to a constraint that there are other competing objectives. For instance, if achieving one lifestyle element amount 724 by selecting from each lifestyle element 728 may result in needing to select a second lifestyle element 728, wherein each may compete in degradation prevention (e.g. adopting two or more diet types simultaneously may not be feasible, a vegan option and a non-vegan option, and the like). A mathematical solver may be implemented to solve for the set of instructions that maximizes scores; mathematical solver may be implemented on computing device 704 and/or another device in system 700, and/or may be implemented on third-party solver.

With continued reference to FIG. 7, objective function may include minimizing a loss function, where a "loss function" is an expression of an output of which a process minimizes to generate an optimal result. For instance, achieving lifestyle element amounts 732 may be set to a nominal value, such as '100', wherein the objective function selects elements in combination that reduce the value to '0', wherein the lifestyle element amounts 732 are '100% achieved'. In such an example, 'maximizing' would be selecting the combination of lifestyle elements 728 that results in achieving lifestyle element amounts 732 by minimizing the difference. As a non-limiting example, computing device 704 may assign variables relating to a set of parameters, which may correspond to degradation prevention components, calculate an output of mathematical expression using the variables, and select an objective that produces an output having the lowest size, according to a given definition of "size." Selection of different loss functions may result in identification of different potential combinations as generating minimal outputs, and thus 'maximizing' efficacy of the combination.

Continuing in reference to FIG. 7, generating body degradation reduction program 740 may include generating a degradation program classifier using a degradation program classification machine-learning process to classify lifestyle elements 728 to the plurality of lifestyle element amounts 732, and outputting the plurality of lifestyle elements 728 as a function of the degradation program classifier. Degradation program classifier may include any classifier, as described above, generated by a classification machine-learning process using training data, performed by a machine-learning module as described in further detail below. Training data for degradation program classifier may include sets of data entries that include lifestyle elements 728 that may be correlated to lifestyle element amounts 732 that degradation classifier 724 may be trained to automatedly locate, sort, and output lifestyle elements 728 according to calculated lifestyle element amounts 732 for the user. Such training data may originate via a database, the Internet, research repository, and the like, as described above for training data for other machine-learning processes. Training data may include foods, supplements, probiotics, nutraceuticals, and the like, correlated to nutrition facts, medicinal qualities, and the like, which a classifier may be trained to locate relationships that aid in locating nutrition elements 728. Degradation program classifier may accept an input of lifestyle element amounts 732 and output a plurality of lifestyle elements 728 with associated frequency (timing) and magnitude (serving size) schedule according to relationships between lifestyle elements 728 and lifestyle element amounts 732. For instance and without limitation, degradation program classifier may identify relationships between individual lifestyle elements, that when more activities are selected, certain activities may not be necessary to schedule within the same timeframe. Such a classification process may determine a function, system of equations, and the like, which can be solved for in determining which lifestyle elements 728 are useful toward obtaining the lifestyle element amounts 732, while not missing some lower limits of lifestyle element amounts 732 and not exceeding upper limits for other lifestyle element amounts 732.

Continuing in reference to FIG. 7, body degradation reduction program includes a body degradation score. A body degradation score may reflect the level of user participation in the body degradation reduction program 740 and the level of body degradation in the user as a function of adherence to body degradation reduction program 740. Body degradation score may include a numerical value, metric, parameter, and the like, described by a function, vector, matrix, or any other mathematical arrangement. Body degradation score 748 may include enumerating a user's current nourishment as it relates to body degradation alleviation, degradation rate, and/or degradation prevention. Generating body degradation score 748 may include using a machine-learning process, algorithm, and/or model to derive a numerical scale along which to provide a numerical value according to a user's body degradation profile 712 and participation in body degradation reduction program 740 generated from body degradation profile 712. For instance, such a machine-learning model may be trained with training data, wherein training data contains data entries of lifestyle element amounts 732 correlated to degradation prevention. Such a machine-learning model may be trained with said training data to be used by computing device 704 to correlate the consumption of particular foods in body degradation reduction program 740 to achieving some level of lifestyle element amount 732, and how the lifestyle element amount 732 relates to body degradation alleviation, degradation rate, and/or degradation prevention. Training data for a machine-learning model for generating body degradation score 748 may include a plurality of data entries including lifestyle element amounts correlated to effects on degradation, wherein the trained model may accept inputs of lifestyle elements a user has engaged in and automatedly determine how the score should increase and/or decrease based on the lifestyle element amount targets for the user. Such training data may originate from any source as descried above, such as a database, web browser and the Internet, physician, peer-reviewed research, and the like.

Continuing in reference to FIG. 7, in non-limiting illustrating examples, falling short of cardio amounts of lifestyle element amounts 732, may have a particular effect on body degradation score 748 for an individual who has been classified to a certain degradation category 720. Where, chronically falling short of the lifestyle element amount 732 results in a (−3) score each month but falling within the lifestyle element amount 732 range for the cardio amounts affords (+1) score for each month; the target amount for the preceding month may dictate the score change for each subsequent month. In such a case, a machine-learning model may derive an algorithm which dictates the amount to increase/decrease body degradation score 748 for that particular degradation category 720 according to the lifestyle element amounts 732. In this case, the machine-learning model is trained to identify the relationship between lifestyle element amounts 732 and effect on degradation reduction to derive an equation that relates scoring criteria. The score is then calculated using the model and lifestyle element data as an input. Engagement by the user may include amounts and identities of lifestyle elements 728. In this way, system 700 may calculate a body degradation score 748 as a function of a user's participation in body degradation reduction program 740, where body degradation score 748 is updated with each lifestyle element 728 consumed by user.

Figure 8:
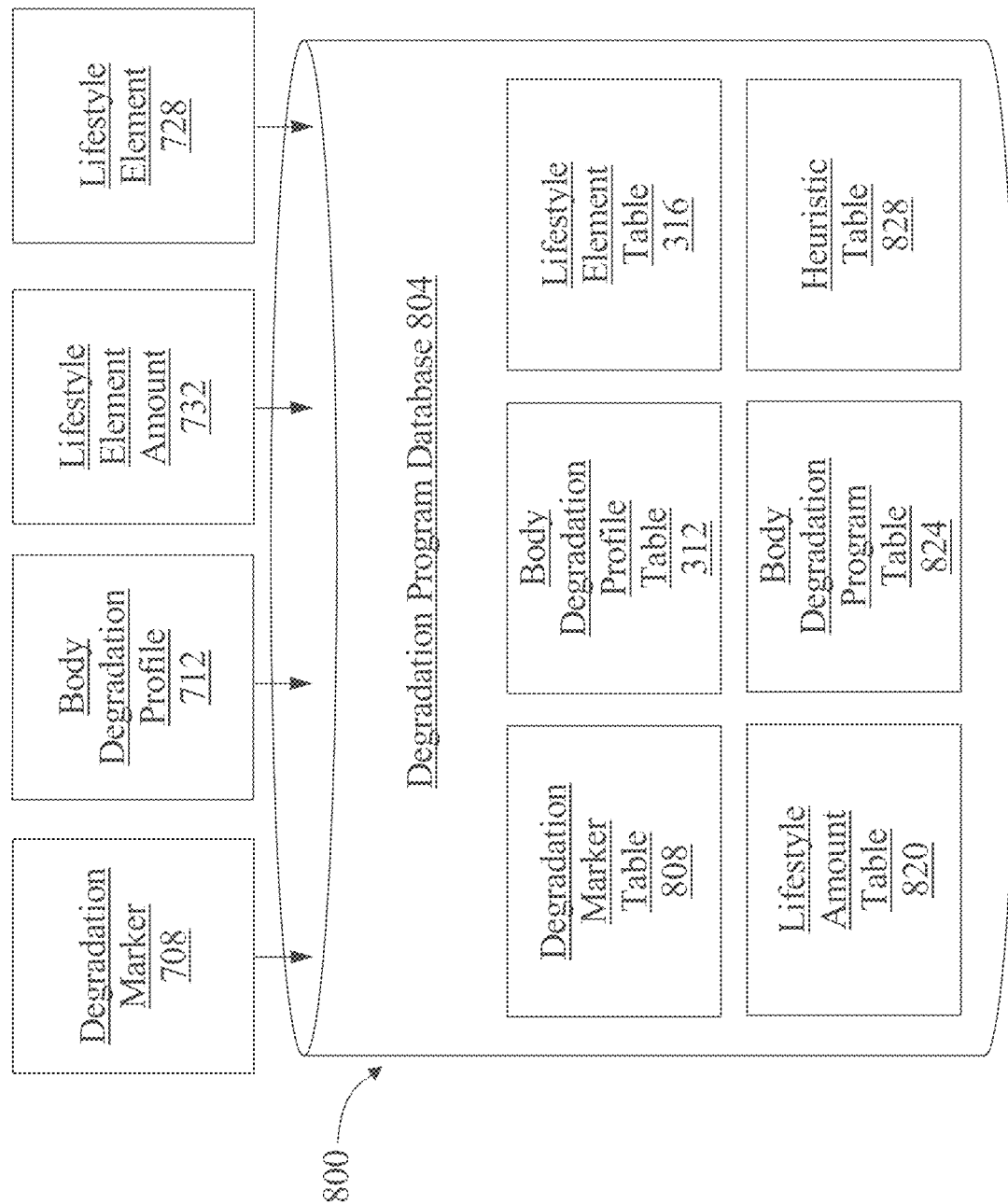
FIG. 8 is a block diagram illustrating a lifestyle element database.

Referring now to FIG. 8, a non-limiting exemplary embodiment 800 of a degradation program database 804 is illustrated. Degradation marker(s) 808 from a plurality of users, for instance for generating a training data classifier 816, may be stored and/or retrieved in degradation program database 304. Degradation marker(s) 808 data from a plurality of users for generating training data may also be stored and/or retrieved from a degradation program database 804. Computing device 704 may receive, store, and/or retrieve training data, wearable device data, physiological sensor data, biological extraction data, and the like, from degradation program database 804. Computing device 704 may store and/or retrieve lifestyle machine-learning model 716, degradation classifier 724, among other determinations, I/O data, models, and the like, from degradation program database 804.

Continuing in reference to FIG. 8, degradation program database 804 may be implemented, without limitation, as a relational database, a key-value retrieval database such as a NOSQL database, or any other format or structure for use as a database that a person skilled in the art would recognize as suitable upon review of the entirety of this disclosure. Degradation program database 804 may alternatively or additionally be implemented using a distributed data storage protocol and/or data structure, such as a distributed hash table and the like. Degradation program database 804 may include a plurality of data entries and/or records, as described above. Data entries in a degradation program database 804 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistent with this disclosure.

Further referring to FIG. 8, degradation program database 804 may include, without limitation, degradation marker table 808, body degradation profile table 812, lifestyle element table 816, lifestyle element amount table 820, body degradation program database 824, and/or heuristic table 828. Determinations by a machine-learning process, machine-learning model, ranking function, and/or classifier, may also be stored and/or retrieved from the degradation program database 804. As a non-limiting example, degradation program database 804 may organize data according to one or more instruction tables. One or more degradation program database 804 tables may be linked to one another by, for instance in a non-limiting example, common column values. For instance, a common column between two tables of degradation program database 804 may include an identifier of a submission, such as a form entry, textual submission, accessory device tokens, local access addresses, metrics, and the like, for instance as defined herein; as a result, a search by a computing device 704 may be able to retrieve all rows from any table pertaining to a given submission or set thereof. Other columns may include any other category usable for organization or subdivision of data, including types of data, names and/or identifiers of individuals submitting the data, times of submission, and the like; persons skilled in the art, upon reviewing the entirety of this disclosure, will be aware of various ways in which data from one or more tables may be linked and/or related to data in one or more other tables.

Continuing in reference to FIG. 8, in a non-limiting embodiment, one or more tables of a degradation program database 804 may include, as a non-limiting example, a degradation marker table 808, which may include categorized identifying data, as described above, including degradation marker 708 data such as genetic data, epigenetic data, microbiome data, physiological data, biological extraction data, and the like. Degradation marker table 808 may include degradation marker 708 categories according to gene expression patterns, SNPs, mutations, enzyme specific activity and concentration, phosphorylation data, proteasomal degradation data, data concerning engagement of lifestyle elements 728, pharmacokinetics, lifestyle element magnitude, and the like, and may include linked tables to mathematical expressions that describe the impact of each degradation marker 708 datum on body degradation profile 712, for instance threshold values for gene expression, and the like, as it relates to degradation parameters, rates, degradation category 720, and the like. One or more tables may include body degradation profile table 812, which may include data regarding degradation marker 708, thresholds, scores, metrics, values, categorizations, and the like, that system 700 may use to calculate, derive, filter, retrieve and/or store current degradation levels, degradation types, symptom-degradation relationships, and the like. One or more tables may include lifestyle element table 816, which may include data on lifestyle elements 728 for instance classified to degradation category 720, classified to data from alike subjects with similar degradation marker 708, body degradation profile 712, and the like, that system 700 may use to calculate, derive, filter, retrieve and/or store lifestyle elements 728. One or more tables may include lifestyle element amount table 820, which may include functions, model, equations, algorithms, and the like, using to calculate or derive lifestyle element amounts 732 relating to body degradation profile 712 and/or degradation category 720, may include lifestyle element amounts 732 organized by lifestyle element, lifestyle element classification, age, sex, degradation severity, and the like. One of more tables may include a body degradation program database 824, which may include lifestyle element 728 identifiers, serving sizes, times associated with lifestyle elements 728 regarding times to engage in an activity, identifiers of activities, regimens, type of activity, schedules and the like. One or more tables may include, without limitation, a heuristic table 828, which may organize rankings, scores, models, outcomes, functions, numerical values, scales, arrays, matrices, and the like, that represent determinations, probabilities, metrics, parameters, values, and the like, include one or more inputs describing potential mathematical relationships, as described herein.

Figure 9:
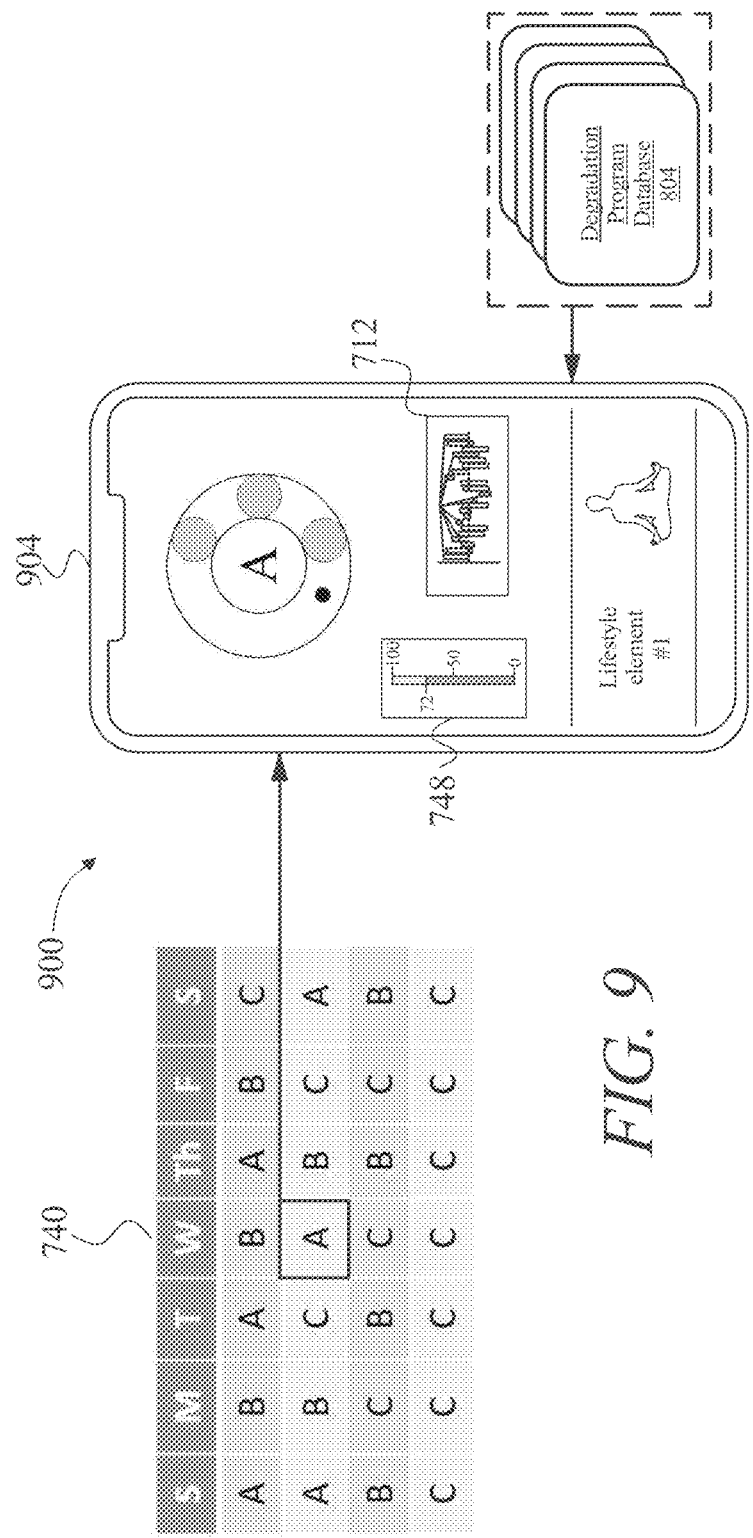
FIG. 9 is a diagrammatic representation of a user device.

Referring now to FIG. 9, a non-limiting exemplary embodiment 900 of a user device 904 is illustrated. User device 904 may include computing device 704, a "smartphone," cellular mobile phone, desktop computer, laptop, tablet computer, internet-of-things (JOT) device, wearable device, among other devices. User device 904 may include any device that is capable for communicating with computing device 704, degradation program database 804, or able to receive, transmit, and/or display, via a graphical user interface, body degradation profile 712, lifestyle element 728, lifestyle body degradation reduction program 740, body degradation score 748, among other outputs from system 700. User device 904 may provide a body degradation profile 712, for instance as a collection of metrics determined from degradation marker 708 data. User device 904 may provide degradation category 720 that was determined as a function of degradation classifier 724 and body degradation profile 712. User device 904 may provide data concerning lifestyle element amounts 732, including the levels of specific lifestyle elements, lifestyle element ranges, lifestyle elements to avoid, and the like. User device 904 may link lifestyle body reduction program 740 to a scheduling application, such as a 'calendar' feature on user device, which may set audio-visual notifications, timers, alarms, and the like.

Figure 10:
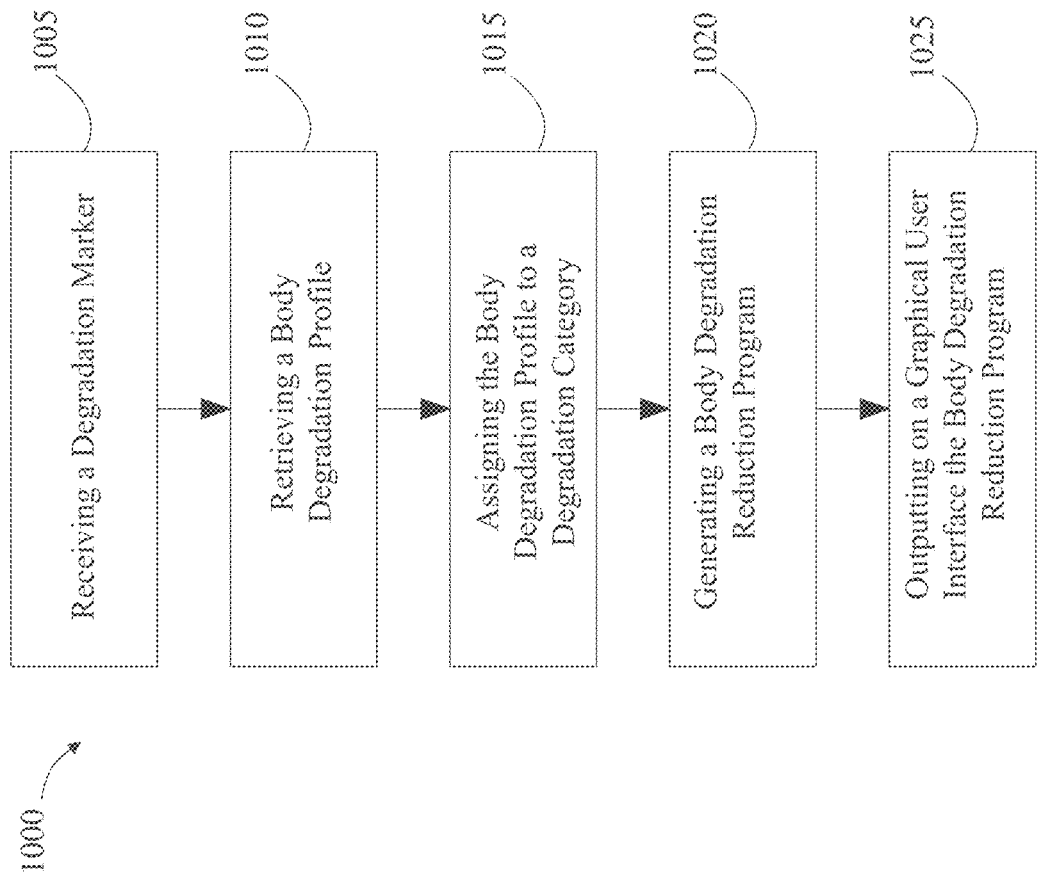
FIG. 10 is a block diagram of a workflow of a method for generating a body degradation reduction program.

Referring now to FIG. 10, an exemplary embodiment of a method 1000 for generating a body degradation reduction program is illustrated. At step 1005 a degradation marker is received from a user. The degradation marker may include biological molecules existing within a normal cell, a stressed cell, disease state cell, and/or a specific response of the body indicative of deterioration and/or aging. Receiving a degradation marker may include receiving a result of one or more tests relating the user. A degradation marker may include test results of screening and/or early detection of degeneration, diagnostic procedures, prognostic indicators from other diagnoses, from predictors identified in a medical history, and physiological data and data relating to biomolecules associated with degradation such as physiological parameters including systolic and diastolic blood pressure, pulse pressure, pulse rate, peak expiratory flow, EKG data; blood metabolites such as homocysteine, creatinine, low-density lipoprotein (LDL), very low density lipoprotein (VLDL), high-density lipoprotein (HDL), triglycerides, fasting glucose, glycosylated hemoglobin (HbA1c); body compositional data including BMI, lean body mass, waist-to-hip ratio; hormonal profile including leptin, adiponectin, testosterone; immunological and disease state indicators such as c-reactive protein, IL-6, fibrinogen, albumin, TNF-α, serum amyloid A, cytomegalovirus, Epstein Barr virus, T cell concentration/ratio, Amyloid B42, Total (t)-Tau, F2-isoprostanes (F2-iso), cortisol, DHEA-S, IGF-1; neurotransmitter concentration and balance such as for norepinephrine, epinephrine; biomarkers of organ function such as cystatin C; indicators of oxidative stress such as reactive oxygen species, superoxide dismutase; genotypic and epigenetic indicators of biological aging such as telomere length; among other data indicative of degradation.

Still referring to FIG. 10, at step 1010, a body degradation profile is retrieved. Body degradation profile may include at least a degradation rate of biological degradation, wherein the degradation level is a relative level of physiological integrity compared to theoretical level of physiological integrity according to what is scientifically achievable for an individual. A degradation rate may include a level of degradation change over time, as an individual ages. A body degradation profile may include at least a degradation rate which may be an instantaneous rate or a rate that is over a variable range of time. A body degradation profile may include biological degradation such as physiological deterioration of, for instance and without limitation, vision, hearing, cardiovascular endurance, maintenance of lean body mass, bone mineral density, short-term memory, mental plasticity, neurodegeneration, telomere length, and the like.

With continued reference to FIG. 10, at step 1015, the body degradation profile is assigned to a degradation category. A degradation category may include a designation of a degradation type. A degradation category may include tissue and/or organ such as "kidney degradation", "liver degradation", "peripheral nervous system degradation", and the like. A degradation category may include a designation regarding a degradation type that may not involve a particular tissue such as "vision degradation", "hearing degradation", "short term memory loss", and the like. A degradation category may include pathological, histological, and/or clinical classification identifiers such as "telomeric length loss of >35 bp/year", "Mini-Mental State Exam (MMSE) score range of 20-24", "myelin sheath thinning", and the like. A degradation category may include identifiers associated with disorders, conditions, symptoms, and the like, which may correspond with categorization. A degradation category may include a predictive degradative classification, where a user such as a healthy young adult, does not harbor degradation marker(s) indicative of obvious current degradation but may include data that indicates a degradation category with which they may be most closely categorized to. For instance, a family history of vision loss as a function of aging due to a combination of epigenetic elements, lifestyle factors, and long-term nutritional impacts, may classify an individual in "vision degradation" degradation category, despite not currently exhibiting lessened vision acuity, astigmatism, or other loss of vision integrity. A body degradation profile may have associated with it an identifier, such as a label, that corresponds to a degradation category. In some embodiments, a degradation category may be stored and/or retrieved from a database.

With continued reference to FIG. 10, at step 1020, a body degradation reduction program is generated. A body degradation reduction program may include a frequency and a magnitude for reducing body degradation of a user revolving around the user's lifestyle. In some embodiments, a body degradation reduction program may include a collection of lifestyle element amounts and lifestyle elements for reducing body degradation of an individual. A body degradation reduction program may be organized into a frequency (timing) and magnitude (intensity of activity) schedule. A frequency may include a number of engagement occurrences associated with a time course, such as daily, weekly, monthly, and the like, of which a lifestyle element is intended to be engaged with. Frequency may be determined as a function of the identified effect, wherein the frequency of engagement may be tailored to provide a sufficient minimal lifestyle element level over a time. A magnitude may include an intensity of an engagement of a lifestyle element as a function of the identified effect. Identifying the magnitude associated with a lifestyle element may include calculating a period of time and intensity of the lifestyle element as a function of the identified effect.

With continued reference to FIG. 1025, the body degradation program is outputted on a graphical user interface. In some embodiments, a body degradation program may be outputted on a user device. A user device may include a "smartphone," cellular mobile phone, desktop computer, laptop, tablet computer, internet-of-things (JOT) device, wearable device, among other devices. A user device may provide a body degradation profile, for instance, as a collection of metrics determined from a degradation marker data. A user device may provide a degradation category that was determined as a function of a degradation classifier and a body degradation profile. A user device may provide data concerning lifestyle element amounts, including the levels of specific lifestyle elements, lifestyle element ranges, lifestyle elements to avoid, and the like. In some embodiments, a user device may link lifestyle body reduction program to a scheduling application, such as a 'calendar' feature on user device, which may set audio-visual notifications, timers, alarms, and the like.

It is to be noted that any one or more of the aspects and embodiments described herein may be conveniently implemented using one or more machines (e.g., one or more computing devices that are utilized as a user computing device for an electronic document, one or more server devices, such as a document server, and the like) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, and the like), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, and the like), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
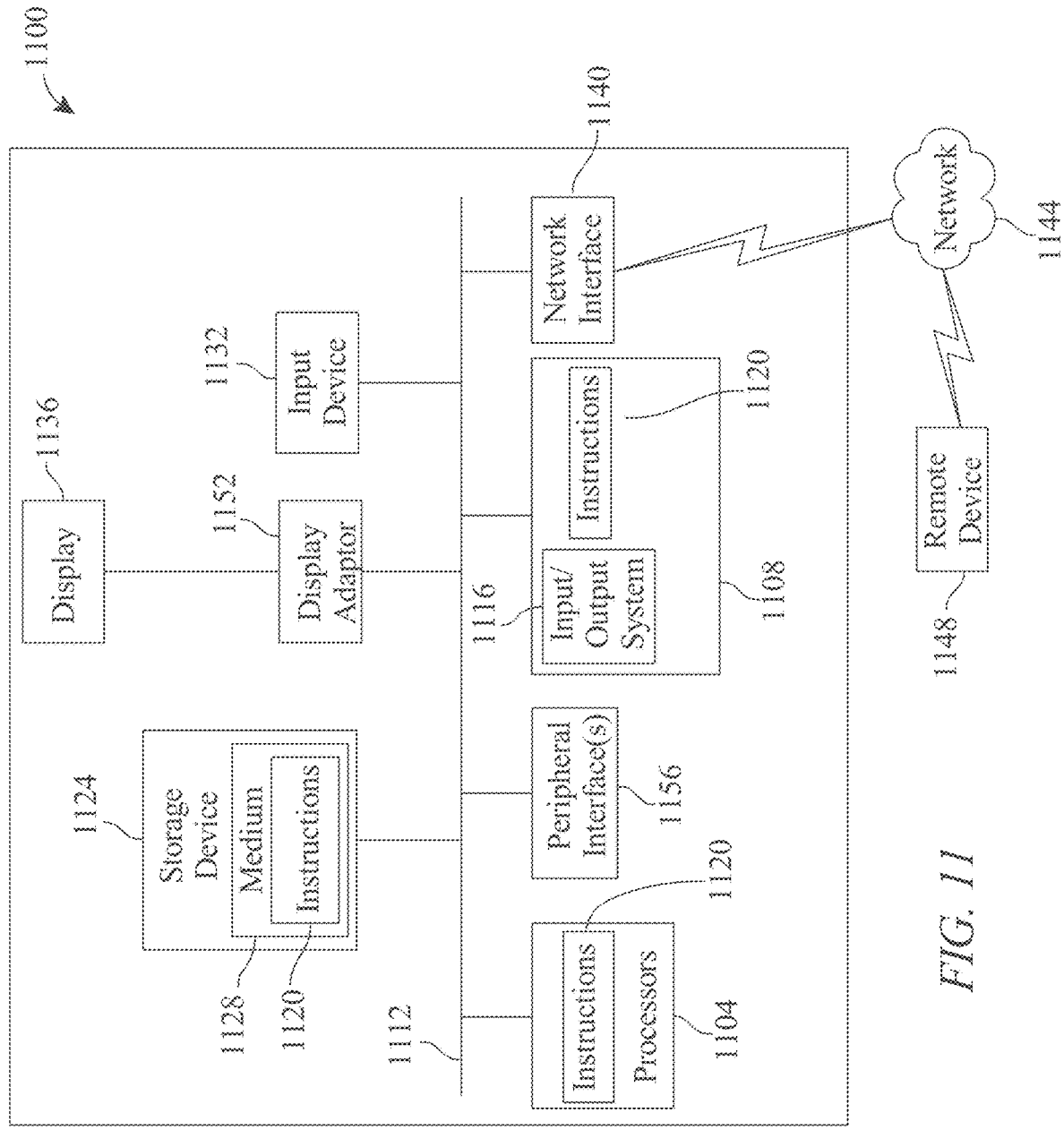
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, and the like), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, and the like) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, and the like) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for generating a body degradation reduction program, the system comprising:
   a computing device, wherein the computing device is configured to:
   receive at least a degradation marker related to a user;
   retrieve a body degradation profile as a function of the at least a degradation marker;
   assign the body degradation profile to a degradation category;
   identify, using the degradation category and the body degradation profile, a plurality of lifestyle elements, wherein identifying the plurality of lifestyle elements includes:
     calculating a plurality of lifestyle element amounts as a function of a respective effect of each of a plurality of lifestyle element amounts on the body degradation profile as a function of the degradation category; and
     identifying the plurality of lifestyle elements as a function of the plurality of lifestyle element amounts;
   generate a body degradation reduction program using the plurality of lifestyle elements, wherein generating the body reduction program includes:
     receiving a plurality of training data comprising lifestyle element amounts and a plurality of correlated effects of each of a plurality of lifestyle element amounts on body degradation profiles of users;
     training a machine learning model as a function of the plurality of training data; and
     generating the body degradation reduction program as a function of the machine-learning model and the plurality of lifestyle elements; and
   output, on a graphical user interface, the body degradation reduction program, wherein the body degradation reduction program includes a frequency of engagement of the plurality of lifestyle elements and a magnitude of engagement of the plurality of lifestyle elements.

2. The system of claim 1, wherein generating the body degradation reduction program includes receiving a user preference and generating the body degradation reduction program as a function of the user preference.

3. The system of claim 2, wherein generating the body degradation reduction program further comprises generating an objective function with the at least a plurality of lifestyle elements wherein the objection function outputs at least an ordering of a plurality of lifestyle elements according to constraints from the degradation category and the user preference.

4. The system of claim 1, wherein the body degradation reduction program includes a body degradation score.

5. The system of claim 1, wherein the plurality of lifestyle elements includes a nutritional element.

6. The system of claim 5, wherein the nutritional element includes a nutritional supplement.

7. The system of claim 1, wherein the plurality of lifestyle elements includes an exercise element.

8. The system of claim 1, wherein the plurality of lifestyle elements includes a mindfulness element comprising meditating.

9. The system of claim 1, wherein the plurality of lifestyle elements includes a spiritual element comprising praying.

10. The system of claim 1, wherein the body degradation reduction program includes a scheduled engagement of a lifestyle activity.

11. A method for generating a body degradation reduction program, the method comprising:
receiving, by a computing device, at least a degradation marker related to a user;
retrieving, by the computing device, a body degradation profile as a function of the at least a degradation marker;
assigning, by the computing device, the body degradation profile to a degradation category;
identifying, by the computing device, using the degradation category and the body degradation profile, a plurality of lifestyle elements, wherein identifying the plurality of lifestyle elements includes:
calculating a plurality of lifestyle element amounts as a function of a respective effect of each of a plurality of lifestyle elements on the body degradation profile as a function of the degradation category; and
identifying the plurality of lifestyle elements as a function of the plurality of lifestyle element amounts;
generating, a body degradation reduction program using the plurality of lifestyle elements, wherein generating the body reduction program includes:
receiving a plurality of training data comprising lifestyle element amounts and a plurality of correlated effects of each of a plurality of lifestyle element amounts on body degradation profiles of users;
training a machine learning model as a function of the plurality of training data; and
generating the body degradation reduction program as a function of the machine-learning model and the plurality of lifestyle elements; and
outputting, on a graphical user interface, the body degradation reduction program, wherein the body degradation reduction program includes a frequency of engagement of the plurality of lifestyle elements and a magnitude of engagement of the plurality of lifestyle elements.

12. The system of claim 11, wherein generating the body degradation reduction program includes receiving a user preference and generating the body degradation reduction program as a function of the user preference.

13. The system of claim 12, wherein generating the body degradation reduction program further comprises generating an objective function with the at least a plurality of lifestyle elements wherein the objection function outputs at least an ordering of a plurality of lifestyle elements according to constraints from the degradation category and the user preference.

14. The system of claim 11, wherein the body degradation reduction program includes a body degradation score.

15. The system of claim 11, wherein the plurality of lifestyle elements includes a nutritional element.

16. The system of claim 15, wherein the nutritional element includes a nutritional supplement.

17. The system of claim 11, wherein the plurality of lifestyle elements includes an exercise element.

18. The system of claim 11, wherein the plurality of lifestyle elements includes a mindfulness element comprising meditating.

19. The system of claim 11, wherein the plurality of lifestyle elements includes a spiritual element comprising praying.

20. The system of claim 11, wherein the body degradation reduction program includes a scheduled engagement of a lifestyle activity.

* * * * *